US006187576B1

(12) United States Patent
Svendsen et al.

(10) Patent No.: US 6,187,576 B1
(45) Date of Patent: Feb. 13, 2001

(54) α-AMYLASE MUTANTS

(75) Inventors: Allan Svendsen, Birkerød; Torben Vedel Borchert, Jyllinge; Henrik Bisgård-Frantzen, Bagsværd, all of (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/170,670

(22) Filed: Oct. 13, 1998

Related U.S. Application Data

(60) Provisional application No. 60/063,306, filed on Oct. 28, 1997.

(30) Foreign Application Priority Data

Oct. 13, 1997 (DK) .................................................. 1172/97

(51) Int. Cl.[7] .............................. C12N 9/00; C12N 9/24; C12N 9/28; C11D 3/00; C11D 7/42

(52) U.S. Cl. .......................... 435/202; 435/183; 435/200; 510/226; 510/235; 510/320; 510/392

(58) Field of Search ............................ 435/96, 98, 172.1, 435/252.3, 202, 220, 201, 204, 440; 536/23.2; 510/226, 235, 320, 392

(56) References Cited

FOREIGN PATENT DOCUMENTS

| | | |
|---|---|---|
| WO 90/11352 | 10/1990 | (WO) . |
| WO 91/00353 | 1/1991 | (WO) . |
| WO 95/10603 | 4/1995 | (WO) . |
| WO 95/26397 | 10/1995 | (WO) . |
| WO 95/35382 | 12/1995 | (WO) . |
| WO 96/23873 | 8/1996 | (WO) . |
| WO 96/23874 | 8/1996 | (WO) . |

OTHER PUBLICATIONS

Gray G.L. et al. Structural genes encoding the thermophilic alpha–amylases of *Bacillus stearothermophilus* and *B.licheniformis*. J.Bacteriol., May 1986, vol. 166(2):635–643.*

* cited by examiner

*Primary Examiner*—Rebecca E. Prouty
*Assistant Examiner*—Manjunath Rao
(74) *Attorney, Agent, or Firm*—Elias J. Lambiris, Esq.; Reza Green, Esq.

(57) ABSTRACT

The invention relates to a variant of a parent Termamyl-like α-amylase, comprising mutations in two, three, four, five or six regions/positions. The variants have increased thermostability at acidic pH and/or at low $Ca^{2+}$ concentrations (relative to the parent). The invention also relates to a DNA construct comprising a DNA sequence encoding an α-amylase variant of the invention, a recombinant expression vector which carries a DNA construct of the invention, a cell which is transformed with a DNA construct of the invention, the use of an α-amylase variant of the invention for washing and/or dishwashing, textile desizing, starch liquefaction, a detergent additive comprising an α-amylase variant of the invention, a manual or automatic dishwashing detergent composition comprising an α-amylase variant of the invention, a method for generating a variant of a parent Termamyl-like α-amylase, which variant exhibits increased thermostability at acidic pH and/or at low $Ca^{2+}$ concentrations (relative to the parent).

22 Claims, 3 Drawing Sheets

```
     1                                                        50
1    HHNGTNGTMM QYFEWHLPND GNHWNRLRDD ASNLRNRGIT AIWIPPAWKG
2    ..NGTNGTMM QYFEWYLPND GNHWNRLRSD ASNLKDKGIS AVWIPPAWKG
3    HHNGTNGTMM QYFEWYLPND GNHWNRLRDD AANLKSKGIT AVWIPPAWKG
4    ....VNGTLM QYFEWYTPND GQHWKRLQND AEHLSDIGIT AVWIPPAYKG
5    ..ANLNGTLM QYFEWYMPND GQHWRRLQND SAYLAEHGIT AVWIPPAYKG
6    .AAPFNGTMM QYFEWYLPDD GTLWTKVANE ANNLSSLGIT ALWLPPAYKG

     51                                                      100
1    TSQNDVGYGA YDLYDLGEFN QKGTVRTKYG TRSQLESAIH ALKNNGVQVY
2    ASQNDVGYGA YDLYDLGEFN QKGTIRTKYG TRNQLQAAVN ALKSNGIQVY
3    TSQNDVGYGA YDLYDLGEFN QKGTVRTKYG TRNQLQAAVT SLKNNGIQVY
4    LSQSDNGYGP YDLYDLGEFQ QKGTVRTKYG TKSELQDAIG SLHSRNVQVY
5    TSQADVGYGA YDLYDLGEFH QKGTVRTKYG TKGELQSAIK SLHSRDINVY
6    TSRSDVGYGV YDLYDLGEFN QKGTVRTKYG TKAQYLQAIQ AAHAAGMQVY

     101                                                     150
1    GDVVMNHKGG ADATENVLAV EVNPNNRNQE ISGDYTIEAW TKFDFPGRGN
2    GDVVMNHKGG ADATEMVRAV EVNPNNRNQE VSGEYTIEAW TKFDFPGRGN
3    GDVVMNHKGG ADGTEIVNAV EVNRSNRNQE TSGEYAIEAW TKFDFPGRGN
4    GDVVLNHKAG ADATEDVTAV EVNPANRNQE TSEEYQIKAW TDFRFPGRGN
5    GDVVINHKGG ADATEDVTAV EVDPADRNRV ISGEHLIKAW THFHFPGRGS
6    ADVVFDHKGG ADGTEWVDAV EVNPSDRNQE ISGTYQIQAW TKFDFPGRGN

     151                                                     200
1    TYSDFKWRWY HFDGVDWDQS RQFQNRIYKF RGDGKAWDWE VDSENGNYDY
2    THSNFKWRWY HFDGVDWDQS RKLNNRIYKF RGDGKGWDWE VDTENGNYDY
3    NHSSFKWRWY HFDGTDWDQS RQLQNKIYKF RGTGKAWDWE VDTENGNYDY
4    TYSDFKWHWY HFDGADWDES RKI.SRIFKF RGEGKAWDWE VSSENGNYDY
5    TYSDFKWHWY HFDGTDWDES RKL.NRIYKF ..QGKAWDWE VSNENGNYDY
6    TYSSFKWRWY HFDGVDWDES RKL.SRIYKF RGIGKAWDWE VDTENGNYDY
```

Fig. 1a

```
    201                                                  250
1   LMYADVDMDH PEVVNELRRW GEWYTNTLNL DGFRIDAVKH IKYSFTRDWL
2   LMYADIDMDH PEVVNELRNW GVWYTNTLGL DGFRIDAVKH IKYSFTRDWS
3   LMYADVDMDH PEVIHELRNW GVWYTNTLNL DGFRIDAVKH IKYSFTRDWL
4   LMYADVDYDH PDVVAETKKW GIWYANELSL DGFRIDAAKH IKFSFLRDWV
5   LMYADIDYDH PDVAAEIKRW GTWYANELQL DGFRLDAVKH IKFSFLRDWV
6   LMYADLDMDH PEVVTELKNW GKWYVNTTNI DGFRLDAVKH IKFSFFPDWL

    251                                                  300
1   THVRNATGKE MFAVAEFWKN DLGALENYLN KTNWNHSVFD VPLHYNLYNA
2   IHVRSATGKN MFAVAEFWKN DLGAIENYLN KTNWNHSVFD VPLHYNFYNA
3   THVRNTTGKP MFAVAEFWKN DLGAIENYLN KTSWNHSAFD VPLHYNLYNA
4   QAVRQATGKE MFTVAEYWQN NAGKLENYLN KTSFNQSVFD VPLHFNLQAA
5   NHVREKTGKE MFTVAEYWQN DLGALENYLN KTNFNHSVFD VPLHYQFHAA
6   SYVRSQTGKP LFTVGEYWSY DINKLHNYIT KTDGTMSLFD APLHNKFYTA

    301                                                  350
1   SNSGGNYDMA KLLNGTVVQK HPMHAVTFVD NHDSQPGESL ESFVQEWFKP
2   SKSGGNYDMR QIFNGTVVQR HPMHAVTFVD NHDSQPEEAL ESFVEEWFKP
3   SNSGGYYDMR NILNGSVVQK HPTHAVTFVD NHDSQPGEAL ESFVQQWFKP
4   SSQGGGYDMR RLLDGTVVSR HPEKAVTFVE NHDTQPGQSL ESTVQTWFKP
5   STQGGGYDMR KLLNGTVVSK HPLKSVTFVD NHDTQPGQSL ESTVQTWFKP
6   SKSGGAFDMR TLMTNTLMKD QPTLAVTFVD NHDTEPGQAL QSWVDPWFKP

    351                                                  400
1   LAYALILTRE QGYPSVFYGD YYGIPTHS.. .VPAMKAKID PILEARQNFA
2   LAYALTLTRE QGYPSVFYGD YYGIPTHG.. .VPAMKSKID PILEARQKYA
3   LAYALVLTRE QGYPSVFYGD YYGIPTHG.. .VPAMKSKID PLLQARQTFA
4   LAYAFILTRE SGYPQVFYGD MYGTKGTSPK EIPSLKDNIE PILKARKEYA
5   LAYAFILTRE SGYPQVFYGD MYGTKGDSQR EIPALKHKIE PILKARKQYA
6   LAYAFILTRQ EGYPCVFYGD YYGIPQYN.. .IPSLKSKID PLLIARRDYA
```

```
     401                                                450
1    YGTQHDYFDH HNIIGWTREG NTTHPNSGLA TIMSDGPGGE KWMYVGQNKA
2    YGRQN..... .......... .......... .......... ..........
3    YGTQHDYFDH HDIIGWTREG NSSHPNSGLA TIMSDGPGGN KWMYVGKNKA
4    YGPQHDYIDH PDVIGWTREG DSSAAKSGLA ALITDGPGGS KRMYAGLKNA
5    YGAQHDYFDH HDIVGWTREG DSSVANSGLA ALITDGPGGA KRMYVGRQNA
6    YGTQHDYLDH SDIIGWTREG GTEKPGSGLA ALITDGPGGS KWMYVGKQHA

     451                                                500
1    GQVWHDITGN KPGTVTINAD GWANFSVNGG SVSIWVKR.. ..........
2    .......... .......... .......... .......... ..........
3    GQVWRDITGN RTGTVTINAD GWGNFSVNGG SVSVWVKQ.. ..........
4    GETWYDITGN RSDTVKIGSD GWGEFHVNDG SVSIYVQ... ..........
5    GETWHDITGN RSEPVVINSE GWGEFHVNGG SVSIYVQR.. ..........
6    GKVFYDLTGN RSDTVTINSD GWGEFKVNGG SVSVWVPRKT TVSTIARPIT

     501               519
1    .......... .........
2    .......... .........
3    .......... .........
4    .......... .........
5    .......... .........
6    TRPWTGEFVR WTEPRLVAW
```

α-AMYLASE MUTANTS

CROSS-REFERENCE TO RELATED APPLICATIONS

The application claims priority under 35 U.S.C 119 of Danish application 1172/97 filed Oct. 13, 1997, and of U.S. provisional application 60/063,306 filed Oct. 28, 1997, the contents of which are fully incorporated herein by reference.

FIELD OF THE INVENTION

The present invention relates, inter alia, to novel variants (mutants) of parent Termamyl-like α-amylases, notably variants exhibiting increased thermostability at acidic pH and/or at low $Ca^{2+}$ concentrations (relative to the parent) which are advantageous with respect to applications of the variants in, industrial starch processing particularly (e.g. starch liquefaction or saccharification).

BACKGROUND OF THE INVENTION

α-Amylases (α-1,4-glucan-4-glucanohydrolases, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of α-amylase such as Termamyl-like α-amylases variants are known from e.g. WO 90/11352, WO 95/10603, WO 95/26397, WO 96/23873 and WO 96/23874.

Among more recent disclosures relating to α-amylases, WO 96/23874 provides three-dimensional, X-ray crystal structural data for a Termamyl-like α-amylase which consists of the 300 N-terminal amino acid residues of the *B. amyloliquefaciens* α-amylase and amino acids 301–483 of the C-terminal end of the *B. licheniformis* α-amylase comprising the amino acid sequence (the latter being available commercially under the tradename Termamyl™), and which is thus closely related to the industrially important Bacillus α-amylases (which in the present context are embraced within the meaning of the term "Termamyl-like α-amylases", and which include, inter alia, the *B. licheniformis, B. amyloliquefaciens* and *B. stearothermophilus* α-amylases). WO 96/23874 further describes methodology for designing, on the basis of an analysis of the structure of a parent Termamyl-like α-amylase, variants of the parent Termamyl-like α-amylase which exhibit altered properties relative to the parent.

WO 95/35382 (Gist Brocades B.V.) concerns amylolytic enzymes derived from *B. licheniformis* with improved properties allowing reduction of the $Ca^{2+}$ concentration under application without a loss of performance of the enzyme. The amylolytic enzyme comprises one or more amino acid changes at positions selected from the group of 104, 128, 187, 188 of the *B. licheniformis* α-amylase sequence.

WO 96/23873 (Novo Nordisk) discloses Termamyl-like α-amylase variants which have increased thermostability obtained by pairwise deletion in the region R181*, G182*, T183* and G184* of the sequence shown in SEQ ID NO: 1 herein.

BRIEF DISCLOSURE OF THE INVENTION

The present invention relates to novel α-amylolytic variants (mutants) of a Termamyl-like α-amylase, in particular variants exhibiting increased thermostability (relative to the parent) which are advantageous in connection with the industrial processing of starch (starch liquefaction, saccharification and the like).

The inventors have surprisingly found out that in case of combining two, three, four, five or six mutations (will be described below), the thermostability of Termamyl-like α-amylases is increased at acidic pH and/or at low $Ca^{2+}$ concentration in comparison to single mutations, such as the mutation disclosed in WO 96/23873 (Novo Nordisk), i.e. pairwise deletion in the region R181*, G182*, T183* and G184* of the sequence shown in SEQ ID NO: 1 herein.

The invention further relates to DNA constructs encoding variants of the invention, to composition comprising variants of the invention, to methods for preparing variants of the invention, and to the use of variants and compositions of the invention, alone or in combination with other α-amylolytic enzymes, in various industrial processes, e.g., starch liquefaction.

BRIEF DESCRIPTION OF THE DRAWING

FIG. 1 is an alignment of the amino acid sequences of six parent Termamyl-like α-amylases in the context of the invention. The numbers on the Extreme left designate the respective amino acid sequences as follows:

1: SEQ ID NO: 2,
2: Kaoamyl,
3: SEQ ID NO: 1,
4: SEQ ID NO: 5,
5: SEQ ID NO: 4,
6: SEQ ID NO: 3.

DETAILED DISCLOSURE OF THE INVENTION

All patents, patent applications, and literature references referred to herein are hereby incorporated by reference in their entirety.

The Termamyl-like α-amylase

It is well known that a number of α-amylases produced by Bacillus spp. are highly homologous on the amino acid level. For instance, the *B. licheniformis* α-amylase comprising the amino acid sequence shown in SEQ ID NO: 4 (commercially available as Termamyl™) has been found to be about 89% homologous with the *B. amyloliquefaciens* α-amylase comprising the amino acid sequence shown in SEQ ID NO: 5 and about 79% homologous with the *B. stearothermophilus* α-amylase comprising the amino acid sequence shown in SEQ ID NO: 3. Further homologous α-amylases include an α-amylase derived from a strain of the Bacillus sp. NCIB 12289, NCIB 12512, NCIB 12513 or DSM 9375, all of which are described in detail in WO 95/26397, and the α-amylase described by Tsukamoto et al., Biochemical and Biophysical Research Communications, 151 (1988), pp. 25–31.

Still further homologous α-amylases include the α-amylase produced by the *B. licheniformis* strain described in EP 0252666 (ATCC 27811), and the α-amylases identified in WO 91/00353 and WO 94/18314. Other commercial Termamyl-like *B. licheniformis* α-amylases are Optitherm™ and Takathe™ (available from Solvay), Maxamyl™ (available from Gist-brocades/Genencor), Spezym AA™ and Spezyme Delta AA™ (available from Genencor), and Keistase™ (available from Daiwa).

Because of the substantial homology found between these α-amylases, they are considered to belong to the same class of α-amylases, namely the class of "Termamyl-like α-amylases".

Accordingly, in the present context, the term "Termamyl-like α-amylase" is intended to indicate an α-amylase which, at the amino acid level, exhibits a substantial homology to Termamyl™, i.e. the *B. licheniformis* α-amylase having the amino acid sequence shown in SEQ ID NO: 4 herein. In other words, a Termamyl-like α-amylase is an α-amylase which has the amino acid sequence shown in SEQ ID NOS: 1, 2, 3, 4, 5, 6, 7 or 8 herein, and the amino acid sequence shown in SEQ ID NO: 1 of WO 95/26397 (the same as the amino acid sequence shown as SEQ ID NO: 7 herein) or in SEQ ID NO: 2 of WO 95/26397 (the same as the amino acid sequence shown as SEQ ID NO: 8 herein) or in Tsukamoto et al., 1988, (which amino acid sequence is shown in SEQ ID NO: 6 herein) or i) which displays at least 60%, preferred at least 70%, more preferred at least 75%, even more preferred at least 80%, especially at least 85%, especially preferred at least 90%, even especially more preferred at least 95% homology with at least one of said amino acid sequences shown in SEQ ID NOS 1 or 2 or 3 or 4 or 5 or 6 or 7 or 8 and/or ii) displays immunological cross-reactivity with an antibody raised against at least one of said α-amylases, and/or iii) is encoded by a DNA sequence which hybridizes to the DNA sequences encoding the above-specified α-amylases which are apparent from SEQ ID NOS: 9, 10, 11, or 12 of the present application (which encoding sequences encode the amino acid sequences shown in SEQ ID NOS: 1, 2, 3, 4 and 5 herein, respectively), from SEQ ID NO: 4 of WO 95/26397 (which DNA sequence, together with the stop codon TAA, is shown in SEQ ID NO: 13 herein and encodes the amino acid sequence shown in SEQ ID NO: 8 herein) and from SEQ ID NO: 5 of WO 95/26397 (shown in SEQ ID NO: 14 herein), respectively.

In connection with property i), the "homology" may be determined by use of any conventional algorithm, preferably by use of the GAP progamme from the GCG package version 7.3 (June 1993) using default values for GAP penalties, which is a GAP creation penalty of 3.0 and GAP extension penalty of 0.1, (Genetic Computer Group (1991) Programme Manual for the GCG Package, version 7, 575 Science Drive, Madison, Wis., USA 53711).

A structural alignment between Termamyl and a Termamyl-like α-amylase may be used to identify equivalent/corresponding positions in other Termamyl-like α-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149–155) and reverse threading (Huber, T; Torda, AE, PROTEIN SCIENCE Vol. 7, No. 1 pp. 142–149 (1998).

Property ii) of the α-amylase, i.e. the immunological cross reactivity, may be assayed using an antibody raised against, or reactive with, at least one epitope of the relevant Termamyl-like like α-amylase. The antibody, which may either be monoclonal or polyclonal, may be produced by methods known in the art, e.g. as described by Hudson et al., Practical Immunology, Third edition (1989), Blackwell Scientific Publications. The immunological cross-reactivity may be determined using assays known in the art, examples of which are Western Blotting or radial immunodiffusion assay, e.g. as described by Hudson et al., 1989. In this respect, immunological cross-reactivity between the α-amylases having the amino acid sequences SEQ ID NOS: 1, 2, 3, 4, 5, 6, 7, or 8 respectively, have been found.

The oligonucleotide probe used in the characterization of the Termamyl-like α-amylase in accordance with property iii) above may suitably be prepared on the basis of the full or partial nucleotide or amino acid sequence of the α-amylase in question.

Suitable conditions for testing hybridization involve pre-soaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes to (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an α-amylase produced or producible by a strain of the organism in question, but also an α-amylase encoded by a DNA sequence isolated from such strain and produced in a host organism transformed with said DNA sequence. Finally, the term is intended to indicate an α-amylase which is encoded by a DNA sequence of synthetic and/or cDNA origin and which has the identifying characteristics of the α-amylase in question. The term is also intended to indicate that the parent α-amylase may be a variant of a naturally occurring α-amylase, i.e. a variant which is the result of a modification (insertion, substitution, deletion) of one or more amino acid residues of the naturally occurring α-amylase.

Parent Hybrid α-amylases

The parent α-amylase may be a hybrid α-amylase, i.e. an α-amylase which comprises a combination of partial amino acid sequences derived from at least two α-amylases.

The parent hybrid α-amylase may be one which on the basis of amino acid homology and/or immunological cross-reactivity and/or DNA hybridization (as defined above) can be determined to belong to the Termamyl-like α-amylase family. In this case, the hybrid α-amylase is typically composed of at least one part of a Termamyl-like α-amylase and part(s) of one or more other α-amylases selected from Termamyl-like α-amylases or non-Termamyl-like α-amylases of microbial (bacterial or fungal) and/or mammalian origin.

Thus, the parent hybrid α-amylase may comprise a combination of partial amino acid sequences deriving from at least two Termamyl-like α-amylases, or from at least one Termamyl-like and at least one non-Termamyl-like bacterial α-amylase, or from at least one Termamyl-like and at least one fungal α-amylase. The Termamyl-like α-amylase from which a partial amino acid sequence derives may, e.g., be any of those specific Termamyl-like α-amylases referred to herein.

For instance, the parent α-amylase may comprise a C-terminal part of an α-amylase derived from a strain of *B. licheniformis*, and a N-terminal part of an α-amylase derived from a strain of *B. amyloliquefaciens* or from a strain of *B. stearothermophilus*. For instance, the parent α-amylase may comprise at least 430 amino acid residues of the C-terminal part of the *B. licheniformis* α-amylase, and may, e.g. comprise a) an amino acid segment corresponding to the 37 N-terminal amino acid residues of the *B. amyloliquefaciens* α-amylase having the amino acid sequence shown in SEQ ID NO: 5 and an amino acid segment corresponding to the 445 C-terminal amino acid residues of the *B. licheniformis* α-amylase having the amino acid sequence shown in SEQ ID No. 4, or b) an amino acid segment corresponding to the 68 N-terminal amino acid residues of the *B. stearothermophilus* α-amylase having the amino acid sequence shown in SEQ ID NO: 3 and an amino acid segment corresponding to the 415 C-terminal amino acid residues of the *B. licheniformis* α-amylase having the amino acid sequence shown in SEQ ID NO: 4.

The non-Termamyl-like α-amylase may, e.g., be a fungal α-amylase, a mammalian or a plant α-amylase or a bacterial α-amylase (different from a Termamyl-like α-amylase). Specific examples of such α-amylases include the *Aspergillus oryzae* TAKA α-amylase, the *A. niger* acid α-amylase, the *Bacillus subtilis* α-amylase, the porcine pancreatic α-amylase and a barley α-amylase. All of these α-amylases have elucidated structures which are markedly different from the structure of a typical Termamyl-like α-amylase as referred to herein.

The fungal α-amylases mentioned above, i.e. derived from *A. niger* and *A. oryzae*, are highly homologous on the amino acid level and generally considered to belong to the same family of α-amylases. The fungal α-amylase derived from *Aspergillus oryzae* is commercially available under the tradename Fungamyl™.

Furthermore, when a particular variant of a Termamyl-like α-amylase (variant of the invention) is referred to—in a conventional manner—by reference to modification (e.g. deletion or substitution) of specific amino acid residues in the amino acid sequence of a specific Termamyl-like α-amylase, it is to be understood that variants of another Termamyl-like α-amylase modified in the equivalent position(s) (as determined from the best possible amino acid sequence alignment between the respective amino acid sequences) are encompassed thereby.

A preferred embodiment of a variant of the invention is one derived from a *B. licheniformis* α-amylase (as parent Termamyl-like α-amylase), e.g. one of those referred to above, such as the *B. licheniformis* α-amylase having the amino acid sequence shown in SEQ ID NO: 4.

Construction of Variants of the Invention

The construction of the variant of interest may be accomplished by cultivating a microorganism comprising a DNA sequence encoding the variant under conditions which are conducive for producing the variant. The variant may then subsequently be recovered from the resulting culture broth. This is described in detail further below.

Altered Properties of Variants of the Invention

The following discusses the relationship between mutations which may be present in variants of the invention, and desirable alterations in properties (relative to those a parent, Termamyl-like α-amylase) which may result therefrom.

Increased Thermostability at Acidic pH and/or at Low $Ca^{2+}$ Concentration

Mutations of particular relevance in relation to obtaining variants according to the invention having increased thermostability at acidic pH and/or at low $Ca^{2+}$ concentration include mutations at the following positions (relative to *B. licheniformis* α-amylase, SEQ ID NO: 4): H156, N172, A181, N188, N190, H205, D207, A209, A210, E211, Q264, N265.

In the context of the invention the term "acidic pH" means a pH below 7.0, especially below the pH range, in which industrial starch liquefaction processes are normally performed, which is between pH 5.5 and 6.2.

In the context of the present invention the term "low Calcium concentration" means concentrations below the normal level used in industrial starch liquefaction. Normal concentrations vary depending of the concentration of free $Ca^{2+}$ in the corn. Normally a dosage corresponding to 1 mM (40 ppm) is added which together with the level in corn gives between 40 and 60 ppm free $Ca^{2+}$.

In the context of the invention the term "high tempertatures" means temperatures between 95° C. and 160° C., especially the temperature range in which industrial starch liquefaction processes are normally performed, which is between 95° C. and 105° C.

The inventors have now found that the thermostability at acidic pH and/or at low $Ca^{2+}$ concentration may be increased even more by combining certain mutations including the above mentioned mutations and/or I201 with each other.

Said "certain" mutations are the following (relative to *B. licheniformis* α-amylase, SEQ ID NO: 4): N190, D207, E211, Q264 and I201.

Said mutation may further be combined with deletions in one, preferably two or even three positions as described in WO 96/23873 (i.e. in positions R181, G182, T183, G184 in SEQ ID NO: 1 herein). According to the invention variants of a parent Termamyl-like α-amylase with α-amylase activity comprising mutations in two, three, four, five or six of the above positions are contemplated.

It should be emphazised that not only the Termamyl-like α-amylases mentioned specifically below are contemplated. Also other commercial Termamyl-like α-amylases are contemplated. An unexhaustive list of such α-amylases is the following: α-amylases produced by the *B. licheniformis* strain described in EP 0252666 (ATCC 27811), and the α-amylases identified in WO 91/00353 and WO 94/18314. Other commercial Termamyl-like *B. licheniformis* α-amylases are Optitherm™ and Takatherm™ (available from Solvay), Maxamyl™ (available from Gist-brocades/Genencor), Spezym AA™ Spezyme Delta AA™ (available from Genencor), and Keistase™ (available from Daiwa).

It may be mentioned here that amino acid residues, respectively, at positions corresponding to N190, I201, D207 and E211, respectively, in SEQ ID NO: 4 constitute amino acid residues which are conserved in numerous Termamyl-like α-amylases. Thus, for example, the corresponding positions of these residues in the amino acid sequences of a number of Termamyl-like α-amylases which have already been mentioned (vide supra) are as follows:

TABLE 1

| Termamyl-like α-amylase | N | I | D | E | Q |
|---|---|---|---|---|---|
| *B. licheniformis* (SEQ ID NO: 4) | N190 | I201 | D207 | E211 | Q264 |
| *B. amyloliquefaciens* (SEQ ID NO: 5) | N190 | V201 | D207 | E211 | Q264 |
| *B. stearothermophilus* (SEQ ID NO: 3) | N193 | L204 | E210 | E214 | — |
| Bacillus WO 95/26397 (SEQ ID NO: 2) | N195 | V206 | E212 | E216 | — |
| Bacillus WO 95/26397 (SEQ ID NO: 1) | N195 | V206 | E212 | E216 | — |
| "Bacillus sp. #707" (SEQ ID NO: 6) | N195 | I206 | E212 | E216 | — |

Mutations of these conserved amino acid residues are very important in relation to improving thermostability at acidic pH and/or at low calcium concentration, and the following mutations are of particular interest in this connection (with reference to the numbering of the *B. licheniformis* amino acid sequence shown in SEQ ID NO: 4).

Pair-wise amino acid deletions at positions corresponding to R179-G182 in SEQ ID NO: 5 corresponding to a gap in Seq ID NO: 4. when aligned with a numerous Termamyl-like α-amylases. Thus, for example, the corresponding positions of these residues in the amino acid sequences of a number of Termamyl-like α-amylases which have already been mentioned (vide supra) are as follows:

TABLE 2

| Termamyl-like α-amylase | Pair wise amino acid deletions among |
|---|---|
| *B. amyloliquefaciens* (SEQ ID No. 5) | R176, G177, E178, G179 |
| *B. stearothermophilus* (SEQ ID No. 3) | R179, G180, I181, G182 |
| Bacillus WO 95/26397 (SEQ ID No. 2) | R181, G182, T183, G184 |
| Bacillus WO 95/26397 (SEQ ID No. 1) | R181, G182, D183, G184 |
| "Bacillus sp. #707" (SEQ ID No. 6) | R181, G182, H183, G184 |

When using SEQ ID NO: 1 to SEQ ID NO: 6 as the backbone (i.e. as the parent Termamyl-like α-amylase) two, three, four, five or six mutations may according to the invention be made in the following regions/positions to increase the thermostability at acidic pH and/or at low $Ca^{2+}$ concentrations (relative to the parent):

(relative to Seq ID NO: 1 herein):
1: R181*, G182*, T183*, G184*
2: N195A,R,D,C,E,Q,G,H,I,L,K,M,F,P,S,T,W,Y,V;
3: V206A,R,D,N,C,E,Q,G,H,I,L,K,M,F,P,S,T,W,Y;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V;

(relative to SEQ ID NO: 2 herein):
1: R181*, G182*, D183*, G184*
2: N195A,R,D,C,E,Q,G,H,I,L,K,M,F,P,S,T,W,Y,V;
3: V206A,R,D,N,C,E,Q,G,H,I,L,K,M,F,P,S,T,W,Y;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V;

(Relative to SEQ ID NO: 3 herein):
1: R179*, G180,I181*, G182*
2: N193A,R,D,C,E,Q,G,H,I,L,K,M,F,P,S,T,W,Y,V;
3: L204A,R,D,N,C,E,Q,G,H,I,K,M,F,P,S,T,W,Y,V;
4: E210A,R,D,N,C,Q,G,H,I,L,K,M,F,P,S,T,W,Y,V;
5: E214A,R,D,N,C,Q,G,H,I,L,K,M,F,P,S,T,W,Y,V;
6: S267A,R,D,N,C,E,Q,G,H,I,L,K,M,F,P,T,W,Y,V Relative to SEQ ID NO: 4 herein):
1: Q178*, G179*
2: N190A,R,D,C,E,Q,G,H,I,L,K,M,F,P,S,T,W,Y,V;
3: I201A,R,D,N,C,E,Q,G,H,L,K,M,F,P,S,T,W,Y,V;
4: D207A,R,N,C,E,Q,G,H,I,L,K,M,F,P,S,T,W,Y,V;
5: E211A,R,D,N,C,Q,G,H,I,L,K,M,F,P,S,T,W,Y,V;
6: Q264A,R,D,N,C,E,G,H,I,L,K,M,F,P,S,T,W,Y,V;

(relative to SEQ ID NO: 5 herein):
1: R176*, G177*, E178,G179*
2: N190A,R,D,C,E,Q,G,H,I,L,K,M,F,P,S,T,W,Y,V;
3: V201A,R,D,N,C,E,Q,G,H,I,L,K,M,F,P,S,T,W,Y;
4: D207A,R,N,C,E,Q,G,H,I,L,K,M,F,P,S,T,W,Y,V;
5: E211A,R,D,N,C,Q,G,H,I,L,K,M,F,P,S,T,W,Y,V;
6: Q264A,R,D,N,C,E,G,H,I,L,K,M,F,P,S,T,W,Y,V;

(relative to SEQ ID NO: 6 herein):
1: R181*, G182*, H183*, G184*
2: N195A,R,D,C,E,Q,G,H,I,L,K,M,F,P,S,T,W,Y,V;
3: I206A,R,D,N,C,E,Q,G,H,L,K,M,F,P,S,T,W,Y,V;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V.

Comtemplated according to the present invention is combining three, four, five or six mutation.

Specific double mutations for backbone SEQ ID NO: 1 to SEQ ID NO: 6 are listed in the following.

Using SEQ ID NO: 1 as the backbone the following double mutantions resulting in the desired effect are comtemplated according to the invention:

-R181*/G182*/N195A,R,D,C,E,Q,G,H,I,L,K,M,F,P,S,T,W,Y,V;
-G182*/T183*/N195A,R,D,C,E,Q,G,H,I,L,K,M,F,P,S,T,W,Y,V;
-G183*/G184*/N195A,R,D,C,E,Q,G,H,I,L,K,M,F,P,S,T,W,Y,V;
-R181*/G182*/V206A,R,D,N,C,E,Q,G,H,I,L,K,M,F,P,S,T,W,Y;
-G182*/T183*/V206A,R, D,N,C,E,Q,G,H,I,L,K,M,F,P,S,T,W,Y;
-T183*/G184*/V206A,R,D,N,C,E,Q,G,H,I,L,K,M,F,P,S,T,W,Y;
-R181*/G182*/E212A,R,D,N,C,Q,G,H,I,L,K,M,F,P,S,T,W,Y,V;
-G182*/T183*/E212A,R,D,N,C,Q,G,H,I,L,K,M,F,P,S,T,W,Y,V;
-T183*/G184*/E212A,R,D,N,C,Q,G,H,I,L,K,M,F,P,S,T,W,Y,V:
-R181*/G182*/E216A,R,D,N,C,Q,G,H,I,L,K,M,F,P,S,T,W,Y,V;
-G182*/T183*/E216A,R,D,N,C,Q,G,H,I,L,K,M,F,P,S,T,W,Y,V;
-T183*/G184*/E216A,R,D,N,C,Q,G,H,I,L,K,M,F,P,S,T,W,Y,V;
-R181*/G182*/K269A,R,D,N,C,E,Q,G,H,I,L,M,F,P,S,T,W,Y,V;
-G182*/T183*/K269A,R,D,N,C,E,Q,G,H,I,L,M,F,P,S,T,W,Y,V;
-T183*/G184*/K269A,R,D,N,C,E,Q,G,H,I,L,M,F,P,S,T,W,Y,V;
-N195A,R,D,C,E,Q,G,H,I,L,K,M,F,P,S,T,W,Y,V/V206A,R,D,N,C,E,Q,G,H,I,L,K,M,F,P,S,T,W,Y;
-N195A,R,D,C,E,Q,G,H,I,L,K,M,F,P,S,T,W,Y,V/E212A,R,D,N,C,Q,G,H,I,L,K,M,F,P,S,T,W,Y,V;
-N195A,R,D,C,E,Q,G,H,I,L,K,M,F,P,S,T,W,Y,V/E216A,R,D,N,C,Q,G,H,I,L,K,M,F,P,S,T,W,Y,V;
-N195A,R,D,C,E,Q,G,H,I,L,K,M,F,P,S,T,W,Y,V/K269A,R,D,N,C,E,Q,G,H,I,L,M,F,P,S,T,W,Y,V;
-V206A,R,D,N,C,E,Q,G,H,I,L,K,M,F,P,S,T,W,Y/E212A,R,D,N,C,Q,G,H,I,L,K,M,F,P,S,T,W,Y,V;
-V206A,R,D,N,C,E,Q,G,H,I,L,K,M,F,P,S,T,W,Y/E216A,R,D,N,C,Q,G,H,I,L,K,M,F,P,S,T,W,Y,V;
-V206A,R,D,N,C,E,Q,G,H,I,L,K,M,F,P,S,T,W,Y/K269A,R,D,N,C,E,Q,G,H,I,L,M,F,P,S,T,W,Y,V;
-E212A,R,D,N,C,Q,G,H,I,L,K,M,F,P,S,T,W,Y,V/E216A,R,D,N,C,Q,G,H,I,L,K,M,F,P,S,T,W,Y,V;
E212A,R,D,N,C,Q,G,H,I,L,K,M,F,P,S,T,W,Y,V/K269A,R,D,N,C,E,Q,G,H,I,L,M,F,P,S,T,W,Y,V;
-E216A,R,D,N,C,Q,G,H,I,L,K,M,F,P,S,T,W,Y,V/K269A,R,D,N,C,E,Q,G,H,I,L,M,F,P,S,T,W,Y,V;

Using SEQ ID NO: 2 as the backbone the following double mutantions resulting in the desired effect are comtemplated according to the invention:

-R181*/G182*/N195A,R,D,C,E,Q,G,H,I,L,K,M,F,P,S,T,W,Y,V;
-G182*/D183*/N195A,R,D,C,E,Q,G,H,I,L,K,M,F,P,S,T,W,Y,V;
-D183*/G184*/N195A,R,D,C,E,Q,G,H,I,L,K,M,F,P,S,T,W,Y,V;
-R181*/G182*/V206A,R,D,N,C,E,Q,G,H,I,L,K,M,F,P,S,T,W,Y;
-G182*/T183*/V206A,R,D,N,C,E,Q,G,H,I,L,K,M,F,P,S,T,W,Y;
-G183*/G184*/V206A,R,D,N,C,E,Q,G,H,I,L,K,M,F,P,S,T,W,Y;
-R181*/G182*/E212A,R,D,N,C,Q,G,H,I,L,K,M,F,P,S,T,W,Y,V;

-G182*/T183*/E212A,R,D,N,C,Q,G,H,I,L,K,M,F,P,S,T,W,Y,V;
-T183*/G184*/E212A,R,D,N,C,Q,G,H,I,L,K,N,F,P,S,T,W,Y,V;
-R181*/G182*/E216A,R,D,N,C,Q,G,H,I,L,K,M,F,P,S,T,W,Y,V;
-G182*/T183*/E216A,R,D,N,C,Q,G,H,I,L,K,M,F,P,S,T,W,Y,V;
-T183*/G184*/E216A,R,D,N,C,Q,G,H,I,L,K,M,F,P,S,T,W,Y,V;
-R181*/G182*/K269A,R,D,N,C,E,Q,G,H,I,L,M,F,P,S,T,W,Y,V;
-G182*/T183*/K269A,R,D,N,C,E,Q,G,H,I,L,M,F,P,S,T,W,Y,V;
-T183*/G184*/K269A,R,D,N,C,E,Q,G,H,I,L,M,F,P,S,T,W,Y,V;
-N195 A,R,D,C,E,Q,G,H,I,L,K,M,F,P,S,T,W,Y,V/V206A,R,D,N,C,E,Q,G,H,I,L,K,M,F,P,S,T,W,Y;
-N195 A,R,D,C,E,Q,G,H,I,L,K,M,F,P,S,T,W,Y,V/E212A,R,D,N,C,Q,G,H,I,L,K,M,F,P,S,T,W,Y,V;
-N/95A,R,D,C,E,Q,G,H,I,L,K,M,F,P,S,T,W,Y,V/E216A,R,D,N,C,Q,G,H,I,L,K,M,F,P,S,T,W,Y,V;
-N195A,R,D,C,E,Q,G,H,I,L,K,M,F,P,S,T,W,Y,V/K269A,R,D,N,C,E,Q,G,H,I,L,M,F,P,S,T,W,Y,V;
-V216A,R,D,N,C,E,Q,G,H,I,L,K,M,F,P,S,T,W,Y/E212A,R,D,N,C,Q,G,H,I,L,K,M,F,P,S,T,W,Y,V;
-V206 A,R,D,N,C,E,Q,G,H,I,L,K,M,F,P,S,T,W,V,Y/E216A,R,D,N,C,Q,G,H,I,L,K,M,F,P,S,T,W,Y,V;
-V206A,R,D,N,C,E,Q,G,H,I,L,K,M,F,P,S,T,W,Y/K269A,R,D,N,C,E,Q,G,H,I,L,M,F,P,S,T,W,Y,V;
-E212A,R,D,N,C,Q,G,H,I,L,K,M,F,P,S,T,W,Y,V/E216A,R,D,N,C,Q,G,H,I,L,K,M,F,P,S,T,W,Y,V;
-E212A,R,D,N,C,Q,G,H,I,L,K,M,F,P,S,T,W,Y,V/K269A,R,D,N,C,E,Q,G,H,I,L,M,F,P,S,T,W,Y,V;
-E216A,R,D,N,C,Q,G,H,I,L,K,M,F,P,S,T,W,Y,V/K269A,R,D,N,C,E,Q,G,H,I,L,M,F,P,S,T,W,Y,V;

Using SEQ ID NO. 3 as the backbone the following double mutantions resulting in the desired effect are comtemplated according to the invention:

-R179*/G180*/N193A,R,D,C,E,Q,G,H,I,L,K,M,F,P,S,T,W,Y,V;
-I180*/I181*/N193A,R,D,C,E,Q,G,H,I,L,K,M,F,P,S,T,W,Y,V;
-I181*/G182*/N193A,R,D,C,E,Q,G,H,I,L,K,M,F,P,S,T,W,Y,V;
-R179*/G180*/L204A,R,D,N,C,E,Q,G,H,I,K,M,F,P,S,T,W,Y,V;
-G180*/I181*/L204A,R,D,N,C,E,Q,G,H,I,K,M,F,P,S,T,W,Y,V;
-I181*/G182*/L204A,R,D,N,C,E,Q,G,H,I,K,M,F,P,S,T,W,Y,V;
-R179*/G180*/E210A,R,D,N,C,Q,G,H,I,L,K,M,F,P,S,T,W,Y,V;
-G180*/I181*/E210A,R,D,N,C,Q,G,H,I,L,K,M,F,P,S,T,W,Y,V;
-I181*/G182*/E210A,R,D,N,C,Q,G,H,I,L,K,M,F,P,S,T,W,Y,V;
-R179*/G180*/E214A,R,D,N,C,Q,G,H,I,L,K,M,F,P,S,T,W,Y,V;
-G180*/I181*/E214A,R,D,N,C,Q,G,H,I,L,K,M,F,P,S,T,W,Y,V;
-I181*/G182*/E214A,R,D,N,C,Q,G,H,I,L,K,M,F,P,S,T,W,Y,V;
-R179*/G180*/S267A,R,D,N,C,E,Q,G,H,I,L,K,M,F,P,T,W,Y,V;
-G180*/I181*/S267A,R,D,N,C,E,Q,G,H,I,L,K,M,F,P,T,W,Y,V;
-I181*/I182*/S267A,R,D,N,C,E,Q,G,H,I,L,K,M,F,P,T,W,Y,V;
-N193A,R,D,C,E,Q,G,H,I,L,K,M,F,P,S,T,W,Y,V/L204A,R,D,N,C,E,Q,G,H,I,K,M,F,P,S,T,W,Y,V;
-N193A,R,D,C,E,Q,G,H,I,L,K,M,F,P,S,T,W,Y,V/E210A,R,D,N,C,Q,G,H,I,L,K,M,F,P,S,T,W,Y,V;
-N193A,R,D,C,E,Q,G,H,I,L,K,M,F,P,S,T,W,Y,V/E214A,R,D,N,C,Q,G,H,I,L,K,M,F,P,S,T,W,Y,V;
-N193A,R,D,C,E,Q,G,H,I,L,K,M,F,P,S,T,W,Y,V/S267A,R,D,N,C,E,Q,G,H,I,L,K,M,F,P,T,W,Y,V;
-L204A,R,D,N,C,E,Q,G,H,I,K,M,F,P,S,T,W,Y,V/E210A,R,D,N,C,Q,G,H,I,L,K,M,F,P,S,T,W,Y,V;
-L204A,R,D,N,C,E,Q,G,H,I,K,M,F,P,S,T,W,Y,V/E214A,R,D,N,C,Q,G,H,I,L,K,M,F,P,S,T,W,Y,V;
-L204A,R,D,N,C,E,Q,G,H,I,K,M,F,P,S,T,W,Y,V/S267A,R,D,N,C,E,Q,G,H,I,L,K,M,F,P,T,W,Y,V;
-E210A,R,D,N,C,Q,G,H,I,L,K,M,F,P,S,T,W,Y,V/E216A,R,D,N,C,Q,G,H,I,L,K,M,F,P,S,T,W,Y,V;
-E210A,R,D,N,C,Q,G,H,I,L,K,M,F,P,S,T,W,Y,V/S267A,R,D,N,C,E,Q,G,H,I,L,K,M,F,P,T,W,Y,V;
-E214A,R,D,N,C,Q,G,H,I,L,K,M,F,P,S,T,W,Y,V/S267A,R,D,N,C,E,Q,G,H,I,L,K,M,F,P,T,W,Y,V;

Using SEQ ID NO. 4 as the backbone the following double mutantions resulting in the desired effect are comtemplated according to the invention:

-Q178*/G179*/N190A,R,D,C,E,Q,G,H,I,L,K,M,F,P,S,T,W,Y,V;
-Q178*/G179*/I201A,R,D,N,C,E,Q,G,H,L,K,M,F,P,S,T,W,Y,V;
-Q178*/G179*/D207A,R,N,C,E,Q,G,H,I,L,K,M,F,P,S,T,W,Y,V;
-Q178*/G179*/E201A,R,D,N,C,Q,G,H,I,L,K,M,F,P,S,T,W,Y,V;
-R179*/G179*/Q264A,R,D,N,C,E,G,H,I,L,K,M,F,P,S,T,W,Y,V;
-N190/I201A,R,D,N,C,E,Q,G,H,L,K,N,F,P,S,T,W,Y,V;
-N190/D207A,R,N,C,E,Q,G,H,I,L,K,M,F,P,S,T,W,Y,V;
-N190/E201A,R,D,N,C,Q,G,H,I,L,K,M,F,P,S,T,W,Y,V;
-N190/Q264A,R,D,N,C,E,G,H,I,L,K,N,F,P,S,T,W,Y,V;
-N201/D207A,R,N,C,Q,E,G,H,I,L,K,M,F,P,S,T,W,Y,V;
-I201/E211A,R,D,N,C,Q,G,H,I,L,K,M,F,P,S,T,W,Y,V;
-I201/Q264A,R,D,N,C,E,G,H,I,L,K,M,F,P,S,T,W,Y,V;
-D207/E211A,R,D,N,C,Q,G,H,I,L,K,M,F,P,S,T,W,Y,V;
-D207/Q264A,R,D,N,C,E,G,H,I,L,K,M,F,P,S,T,W,Y,V;
-E211/Q264A,R,D,N,C,E,G,H,I,L,K,M,F,P,S,T,W,Y,V;

Using SEQ ID NO: 5 as the backbone the following double mutantions resulting in the desired effect are comtemplated according to the invention:

-R176*/G177*/N190A,R,D,C,E,Q,G,H,I,L,K,M,F,P,S,T,W,Y,V;
-G177*/E178*/N190A,R,D,C,E,Q,G,H,I,L,K,M,F,P,S,T,W,Y,V;
-E178*/G179*/N190A,R,D,C,E,Q,G,H,I,L,K,M,F,P,S,T,W,Y,V;
-R176*/G177*/V201A,R,D,N,C,E,Q,G,H,I,L,K,M,F,P,S,T,W,Y;
-G176*/E178*/V201A,R,D,N,C,E,Q,G,H,I,L,K,M,F,P,S,T,W,Y;
-E178*/G179*/V201A,R,D,N,C,E,Q,G,H,I,L,K,M,F,P,S,T,W,Y;
-R176*/G177*/D207A,R,N,C,E,Q,G,H,I,L,K,M,F,P,S,T,W,Y,V;
-G177*/E178*/D207A,R,N,C,E,Q,G,H,I,L,K,M,F,P,S,T,W,Y,V;
-E178*/G179*/D207A,R,N,C,E,Q,G,H,I,L,K,M,F,P,S,T,W,Y,V;
-R176*/G177*/E211A,R,D,N,C,Q,G,H,I,L,K,M,F,P,S,T,W,Y,V;

-G177*/E178*/E211A,R,D,N,C,Q,G,H,I,L,K,M,F,P,S,T,W,Y,V;

-E178*/G179*/E211A,R,D,N,C,Q,G,H,I,L,K,M,F,P,S,T,W,Y,V;

-R176*/G177*/Q264A,R,D,N,C,E,G,H,I,L,K,M,F,P,S,T,W,Y,V;

-G177*/E178*/Q264A,R,D,N,C,E,G,H,I,L,K,M,F,P,S,T,W,Y,V;

-E178*/G179*/Q264A,R,D,N,C,E,G,H,I,L,K,M,F,P,S,T,W,Y,V;

-N190A,R,D,C,E,Q,G,H,I,L,K,M,F,P,S,T,W,Y,V/V201A,R,D,N,C,E,Q,G,H,I,L,K,M,F,P,S,T,W,Y;

-N190A,R,D,C,E,Q,G,H,I,L,K,M,F,P,S,T,W,Y,V/D207A,R,N,C,E,Q,G,H,I,L,K,M,F,P,S,T,W,Y,V;

-N190A,R,D,C,E,Q,G,H,I,L,K,M,F,P,S,T,W,Y,V/E211A,R,D,N,C,Q,G,H,I,L,K,M,F,P,S,T,W,Y,V;

-N190A,R,D,C,E,Q,G,H,I,L,K,M,F,P,S,T,W,Y,V/Q264A,R,D,N,C,E,G,H,I,L,K,M,F,P,S,T,W,Y,V;

-V201A,R,D,N,C,E,Q,G,H,I,L,K,M,F,P,S,T,W,Y/D207A,R,N,C,E,Q,G,H,I,L,K,M,F,P,S,T,W,Y,V;

-V201A,R,D,N,C,E,Q,G,H,I,L,K,M,F,P,S,T,W,Y/E211A,R,D,N,C,Q,G,H,I,L,K,M,F,P,S,T,W,Y,V;

-V201A,R,D,N,C,E,Q,G,H,I,L,K,M,F,P,S,T,W,Y/Q264A,R,D,N,C,E,G,H,I,L,K,M,F,P,S,T,W,Y,V;

-D207A,R,N,C,E,Q,G,H,I,L,K,M,F,P,S,T,W,Y,V/E211A,R,D,N,C,Q,G,H,I,L,K,M,F,P,S,T,W,Y,V;

-D207A,R,N,C,E,Q,G,H,I,L,K,M,F,P,S,T,W,Y,V/Q264A,R,D,N,C,E,G,H,I,L,K,M,F,P,S,T,W,Y,V;

-E211A,R,D,N,C,Q,G,H,I,L,K,M,F,P,S,T,W,Y,V/Q264A,R,D,N,C,E,G,H,I,L,K,M,F,P,S,T,W,Y,V.

Using SEQ ID NO: 6 as the backbone the following double mutantions resulting in the desired effect are contemplated according to the invention:

-R181*/G182*/N195A,R,D,C,E,Q,G,H,I,L,K,M,F,P,S,T,W,Y,V;

-G182*/H183*/N195A,R,D,C,E,Q,G,H,I,L,K,M,F,P,S,T,W,Y,V;

-H183*/G184*/N195A,R,D,C,E,Q,G,H,I,L,K,M,F,P,S,T,W,Y,V;

-R181*/G182*/I206A,R,D,N,C,E,Q,G,H,L,K,M,F,P,S,T,W,Y,V;

-G182*/H183*/I206A,R,D,N,C,E,Q,G,H,L,K,M,F,P,S,T,W,Y,V;

-H183*/G184*/I206A,R,D,N,C,E,Q,G,H,L,K,M,F,P,S,T,W,Y,V;

-R181*/G182*/E212A,R,D,N,C,Q,G,H,I,L,K,M,F,P,S,T,W,Y,V;

-G182*/H183*/E212A,R,D,N,C,Q,G,H,I,L,K,M,F,P,S,T,W,Y,V;

-H183*/G184*/E212A,R,D,N,C,Q,G,H,I,L,K,M,F,P,S,T,W,Y,V;

-R181*/G182*/E216A,R,D,N,C,Q,G,H,I,L,K,M,F,P,S,T,W,Y,V;

-G182*/H183*/E216A,R,D,N,C,Q,G,H,I,L,K,M,F,P,S,T,W,Y,V;

-H183*/G184*/E216A,R,D,N,C,Q,G,H,I,L,K,M,F,P,S,T,W,Y,V;

-R181*/G182*/K269A,R,D,N,C,E,Q,G,H,I,L,M,F,P,S,T,W,Y,V;

-G182*/H183*/K269A,R,D,N,C,E,Q,G,H,I,L,M,F,P,S,T,W,Y,V;

-H183*/G184*/K269A,R,D,N,C,E,Q,G,H,I,L,M,F,P,S,T,W,Y,V;

-N195A,R,D,C,E,Q,G,H,I,L,K,M,F,P,S,T,W,Y,V/I206A,R,D,N,C,E,Q,G,H,L,K,M,F,P,S,T,W,Y,V;

-N195A,R,D,C,E,Q,G,H,I,L,K,M,F,P,S,T,W,Y,V/E212A,R,D,N,C,Q,G,H,I,L,K,M,F,P,S,T,W,Y,V;

/N195A,R,D,C,E,Q,G,H,I,L,K,M,F,P,S,T,W,Y,V/E216A,R,D,N,C,Q,G,H,I,L,K,M,F,P,S,T,W,Y,V;

-N195A,R,D,C,E,Q,G,H,I,L,K,M,F,P,S,T,W,Y,V/K269A,R,D,N,C,E,Q,G,H,I,L,M,F,P,S,T,W,Y,V;

-I206A,R,D,N,C,E,Q,G,H,L,K,M,F,P,S,T,W,Y,V/E212A,R,D,N,C,Q,G,H,I,L,K,M,F,P,S,T,W,Y,V;

-I206A,R,D,N,C,E,Q,G,H,L,K,M,F,P,S,T,W,Y,V/E216A,R,D,N,C,Q,G,H,I,L,K,M,F,P,S,T,W,Y,V;

-I206A,R,D,N,C,E,Q,G,H,L,K,M,F,P,S,T,W,Y,V/K269A,P,D,N,C,E,Q,C,H,I,L,M,F,P,S,T,W,Y,V;

-E212A,R,D,N,C,Q,G,H,J,L,K,M,F,P,S,T,W,Y,V/E216A,R,D,N,C,Q,G,H,J,L,K,M,F,P,S,T,W,Y,V;

-E212A,R,D,N,C,Q,G,H,I,L,K,M,F,P,S,T,W,Y,V/K269A,R,D,N,C,E,Q,G,H,I,L,M,F,P,S,T,W,Y,V;

-E216A,R,D,N,C,Q,G,H,I,L,K,M,F,P,S,T,W,Y,V/K269A,R,D,N,C,E,Q,G,H,I,L,M,F,P,S,T,W,Y,V;

All Termamyl-like α-amylase defined above may suitably be used as backbone for preparing variants of the invention.

However,in a preferred embodiment the variant comprises the following mutations: N190F/Q264S in SEQ ID NO: 4 or in corresponding positiones in another parent Termamyl-like α-amylases.

In another embodiment the variant of the invention comprises the following mutations: I181*/G182*/N193F in SEQ ID NO: 3 (TVB146) or in corresponding positions in another parent Termamyl-like α-amylases. Said variant may further comprise a substitution in position E214Q.

In a preferred embodiment of the invention the parent Termamyl-like α-amylase is a hybrid α-amylase of SEQ ID NO: 4 and SEQ ID NO: 5. Specifically, the parent hybrid Termamyl-like α-amylase may be a hybrid alpha-amylase comprising the 445 C-terminal amino acid residues of the *B. licheniformis* α-amylase shown in SEQ ID NO: 4 and the 37 N-terminal amino acid residues of the α-amylase derived from *B. amyloliquefaciens* shown in SEQ ID NO: 5, which may suitably further have the following mutations: H156Y+A181T+N190F+A209V+Q264S (using the numbering in SEQ ID NO: 4). The latter mentioned hybrid is used in the examples below and is referred to as LE174.

General Mutations in Variants of the Invention

It may be preferred that a variant of the invention comprises one or more modifications in addition to those outlined above. Thus, it may be advantageous that one or more proline residues present in the part of the α-amylase variant which is modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present among the amino acid residues with which the parent α-amylase is modified is/are replaced with a non-cysteine residue such as serine, alanine, threonine, glycine, valine or leucine.

Furthermore, a variant of the invention may—either as the only modification or in combination with any of the above outlined modifications—be modified so that one or more Asp and/or Glu present in an amino acid fragment corresponding to the amino acid fragment 185–209 of SEQ ID NO: 4 is replaced by an Asn and/or Gln, respectively. Also of interest is the replacement, in the Termamyl-like α-amylase, of one or more of the Lys residues present in an amino acid fragment corresponding to the amino acid fragment 185–209 of SEQ ID NO: 4 by an Arg.

It will be understood that the present invention encompasses variants incorporating two or more of the above outlined modifications.

Furthermore, it may be advantageous to introduce point-mutations in any of the variants described herein.

Methods for Preparing α-amylase Variants

Several methods for introducing mutations into genes are known in the art. After a brief discussion of the cloning of α-amylase-encoding DNA sequences, methods for generating mutations at specific sites within the α-amylase-encoding sequence will be discussed.

Cloning a DNA Sequence Encoding an α-amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced. Another method for introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent α-amylase may be conveniently performed by use of any method known in the art.

In relation to the above, a further aspect of the present invention relates to a method for generating a variant of a parent α-amylase, e.g. wherein the variant exhibits altered or increased thermal stability relative to the parent, the method comprising:

(a) subjecting a DNA sequence encoding the parent α-amylase to random mutagenesis, (b) expressing the mutated DNA sequence obtained in step (a) in a host cell, and (c) screening for host cells expressing an α-amylase variant which has an altered property (i.e. thermal stability) relative to the parent α-amylase.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the α-amylase enzyme by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent α-amylase is subjected to PCR under conditions that increase the mis-incorporation of nucleotides (Deshler 1992; Leung et al., Technique, Vol. 1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the α-amylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent α-amylase. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification mazy be performed in accordance with methods known in the art, the presently preferred method being PCR-generated amiplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli.*

The mutated DNA sequence may further comprise a DNA sequence encoding functions permitting expression of the mutated DNA sequence.

Localized Random Mutagenesis

The random mutagenesis may be advantageously localized to a part of the parent α-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing α-amylase Variants

Alternative methods for providing variants of the invention include gene shuffling method known in the art including the methods e.g. described in WO 95/22625 (from Affymax Technologies N.V.) and WO 96/00343 (from Novo Nordisk A/S).

Expression of α-amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an α-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amiyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase variant of the invention.

Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the Bacillus α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an α-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an α-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favourably be selected from a species of Saccharomryces or Schizosaccharomryces, e.g. *Saccharomyces cerevisiae*. The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In yet a further aspect, the present invention relates to a method of producing an α-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant of the invention. Suitable media are available from commercial suppliers or may be prepared according to published recipes (e.g. as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The α-amylase variants of this invention possesses valuable properties allowing for a variety of industrial applications. In particular, enzyme variants of the invention are applicable as a component in washing, dishwashing and hard-surface cleaning detergent compositions. Numerous variants are particularly useful in the production of sweeteners and ethanol from starch, and/or for textile desizing. Conditions for conventional starch-conversion processes, including starch liquefaction and/or saccharification processes, are described in, e.g., U.S. Pat. No. 3,912,590 and in EP patent publications Nos. 252 730 and 63 909.

Production of Sweeteners from Starch:

A "traditional" process for conversion of starch to fructose syrups normally consists of three consecutive enzymatic processes, viz. a liquefaction process followed by a saccharification process and an isomerization process. During the liquefaction process, starch is degraded to dextrins by an α-amylase (e.g. Termamyl™) at pH values between 5.5 and 6.2 and at temperatures of 95–160° C. for a period of approx. 2 hours. In order to ensure an optimal enzyme stability under these conditions, 1 mM of calcium is added (40 ppm free calcium ions).

After the liquefaction process the dextrins are converted into dextrose by addition of a glucoamylase (e.g. AMG™) and a debranching enzyme, such as an isoamylase or a pullulanase (e.g. Promozyme™). Before this step the pH is reduced to a value below 4.5, maintaining the high temperature (above 95° C.), and the liquefying α-amylase activity is denatured. The temperature is lowered to 60° C., and glucoamylase and debranching enzyme are added. The saccharification process proceeds for 24–72 hours.

After the saccharification process the pH is increased to a value in the range of 6–8, preferably pH 7.5, and the calcium is removed by ion exchange. The dextrose syrup is then converted into high fructose syrup using, e.g., an immmobilized glucoseisomerase (such as Sweetzyme™).

At least 1 enzymatic improvements of this process could be envisaged. Reduction of the calcium dependency of the liquefying α-amylase. Addition of free calcium is required to ensure adequately high stability of the α-amylase, but free calcium strongly inhibits the activity of the glucoseisomerase and needs to be removed, by means of an expensive unit operation, to an extent which reduces the level of free calcium to below 3–5 ppm. Cost savings could be obtained if such an operation could be avoided and the liquefaction process could be performed without addition of free calcium ions.

To achieve that, a less calcium-dependent Termamyl-like α-amylase which is stable and highly active at low concentrations of free calcium (<40 ppm) is required. Such a Termamyl-like α-amylase should have a pH optimum at a pH in the range of 4.5–6.5, preferably in the range of 4.5–5.5.

Detergent Compositions

As mentioned above, variants of the invention may suitably be incorporated in detergent compositions. Increased thermostability at low calcium concentrations would be very beneficial for amylase performance in detergents, i.e. the alkaline region. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a lipase, cutinase, protease, cellulase, peroxidase or laccase, and/or another α-amylase.

α-amylase variants of the invention may be incorporated in detergents at conventionally employed concentrations. It is at present contemplated that a variant of the invention may be incorporated in an amount corresponding to 0.00001–1 mg (calculated as pure, active enzyme protein) of α-amylase per liter of wash/dishwash liquor using conventional dosing levels of detergent.

The invention also relates to a composition comprising a mixture of one or more variants of the invention derived from (as the parent Termamyl-like α-amylase) the *B. stearothermophilus* α-amylase having the sequence shown in SEQ ID NO: 3 and a Termamyl-like alpha-amylase derived from the *B. licheniformis* α-amylase having the sequence shown in SEQ ID NO: 4.

Further, the invention also relates to a composition comprising a mixture of one or more variants according the invention derived from (as the parent Termamyl-like α-amylase) the *B. stearothermophilus* α-amylase having the sequence shown in SEQ ID NO: 3 and a hybrid alpha-amylase comprising a part of the *B. amyloliquefaciens* α-amylase shown in SEQ ID NO: 5 and a part of the *B. licheniformis* α-amylase shown in SEQ ID NO: 4. The latter mentioned hydrid Termamyl-like α-amylase comprises the 445 C-terminal amino acid residues of the *B. licheniformis* α-amylase shown in SEQ ID NO: 4 and the 37 N-terminal amino acid residues of the α-amylase derived from *B. amyloliquefaciens* shown in SEQ ID NO: 5. Said latter mentioned hybrid α-amylase may suitably comprise the following mutations: H156Y+A181T+N190F+A209V+Q264S (using the numbering in SEQ ID NO: 4). In the examples below said hybrid parent Termamyl-like α-amylase, is used in combination with variants of the invention, which variants may be used in compositions of the invention.

In a specific embodiment of the invention the composition comprises a mixture of TVB146 and LE174, e.g., in a ratio of 2:1 to 1:2, such as 1:1.

A α-amylase variant of the invention or a composition of the invention may in an aspect of the invention be used for washing and/or dishwashing; for textile desizing or for starch liquefaction.

MATERIALS AND METHODS

Enzymes:

BSG alpha-amylase: *B. stearothermophilus* alpha-amylase depicted in SEQ ID NO: 3. TVB146 alpha-amylase variant: *B. stearothermophilus* alpha-amylase variant depicted in SEQ ID NO: 3 with the following mutations: with the deletion in positions I181-G182+N193F. LE174 hybrid alpha-amylase variant: LE174 is a hybrid Termamyl-like alpha-amylase being identical to the Termamyl sequence, i.e., the *Bacillus licheniformis* α-amylase shown in SEQ ID NO: 4, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 5, which further have following mutations: H156Y+A181T+N190F+A209V+Q264S (using the numbering in SEQ ID NO: 4). LE174 was constructed by SOE-PCR (Higuchi et al. 1988, Nucleic Acids Research 16:7351).

Fermentation and Purification of α-amylase Variants

A *B. subtilis* strain harbouring the relevant expression plasmid is streaked on a LB-agar plate with 10 μg/ml kanamycin from −80° C. stock, and grown overnight at 37° C. The colonies are transferred to 100 ml BPX media supplemented with 10 μg/ml kanamycin in a 500 ml shaking flask.

| Composition of BPX medium: | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20–25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris, pH 9.0 and applied on a Q-sepharose F.F. and eluted with a linear gradient from 0–0.3M NaCl over 6 column volumes. The fractions which contain the activity (measured by the Phadebas assay) are pooled, pH was adjusted to pH 7.5 and remaining color was removed by a treatment with 0.5% W/vol. active coal in 5 minutes.

Activity Determination—(KNU)

One Kilo alpah-amylase Unit (1 KNU) is the amount of enzyme which breaks down 5.26 g starch (Merck, Amylum Solubile, Erg. B 6, Batch 9947275) per hour in Novo Nordisk's standard method for determination of alpha-amylase based upon the following condition:

| | |
|---|---|
| Substrate | soluble starch |
| Calcium content in solvent | 0.0043M |

-continued

| | |
|---|---|
| Reaction time | 7–20 minutes |
| Temperature | 37° C. |
| pH | 5.6 |

Detailed description of Novo Nordisk's analytical method (AF 9) is available on request.

BS-amylase Activity Determination—KNU(S)

1. Application Field

This method is used to determine α-amylase activity in fermentation and recovery samples and formulated and granulated products.

2. Principle

BS-amylase breaks down the substrate (4,6-ethylidene $(G_7)$-p-nitrophenyl $(G_1)$-α,D-maltoheptaoside (written as ethylidene-$G_7$-PNP) into, among other things, $G_2$-PNP and $G_3$-PNP, where G denoted glucose and PNP p-nitrophenol.

G2-PNP and G3-PNP are broken down by α-glucosidase, which is added in excess, into glucose and the yellow-coloured p-nitrophenol.

The colour reaction is monitored in situ and the change in absorbance over time calculated as an expression of the spreed of the reaction and thus of the activity of the enzyme. See the Boehringer Mannheim 1442 309 guidelines for further details.

| 2.1 Reaction conditions | |
|---|---|
| Reaction: | |
| Temperature | 37° C. |
| pH | 7.1 |
| Pre-incubation time | 2 minutes |
| Detection: | |
| Wavelength | 405 nm |
| Measurement time | 3 minutes |

3. Definition of Units

*Bacillus stearothermophius* alpha-amylase (BS-amylase) activity is determined relative to a standard of declared activity and stated in Kilo Novo Units (Stearothermophilus) or KNU(S)).

4. Specificity and Sensitivity

Limit of determination: approx. 0.4 KNU(s)/g

5. Apparatus

Cobas Fara analyser

Diluted (e.g. Hamilton Microlab 1000)

Analytical balance (e.g. Mettler AE 100)

Stirrer plates

6. Reagents/Substrates

A ready-made kit is used in this analysis to determine α-amylase activity. Note that the reagents specified for the substrate and α-glucosidase are not used as described in the Boehringer Mannheim guidelines. However, the designations "buffer", "glass 1", glass 1a" and Glass 2" are those referred to in those guidelines.

6.1. Substrate 4,6-ethylidene$(G_7)$-p-nitrophenyl$(G_1)$-α,D-maltoheptaoside (written as ethylidene-$G_7$-PNP) e.g. Boehringer Mannheim 1442 309

6.2 α-glucosidase help reagent

α-glucosidase, e.g. Boehringer Mannheim 1442 309

| 6.3 BRIJ 35 solution | |
|---|---|
| BRIJ 35 (30% W/V Sigma 430 AG-6) | 1000 mL |
| Demineralized water | up to 2,000 mL |
| 6.4 Stabiliser | |
| Brij 35 solution | 33 mL |
| $CaCl_2*2H_2O$ (Merck 2382) | 882 g |
| Demineralized water | up to 2,000 mL |

7. Samples and Standards 7.1 Standard curve

Example: Preparation of BS-amylase standard curve

The relevant standard is diluted to 0.60 KNU(s)/mL as follows. A calculated quantity of standard is weighed out and added to 200 mL volumetric flask, which is filled to around the ⅔ mark with demineralized water. Stabiliser corresponding to 1% of the volume of the flask is added and the flask is filled to the mark with demineralized water.

A Hamilton Microlab 1000 is used to produce the dilutions shown below. Demineralized water with 1% stabiliser is used as the diluent.

| Dilution No. | Enzyme stock solution | 1% stabiliser | KNU(s)/mL |
|---|---|---|---|
| 1 | 20 μL | 580 μL | 0.02 |
| 2 | 30 μL | 570 μL | 0.03 |
| 3 | 40 μL | 560 μL | 0.04 |
| 4 | 50 μL | 550 μL | 0.05 |
| 5 | 60 μL | 540 μL | 0.06 |

7.2 Level control

A Novo Nordisk A/S BS amylase level control is included in all runs using the Cobas Fara. The control is diluted with 1% stabiliser so that the final dilution is within the range of the standard curve. All weights and dilutions are noted on the worklist 7.3 Sample solutions Single determination Fermentation samples (not final samples) from production, all fermentation samples from pilot plants and storage stability samples are weighed out and analyzed once only.

Double determination over 1 run:

Process samples, final fermentation samples from production, samples from GLP studies and R&D samples are weighed out and analyzed twice.

Double determinations over 2 runs:

Finished product samples are weighed out and analyzed twice over two separate runs.

Maximum concentration of samples in powder form: 5%

Test samples are diluted with demineralized water with 1% stabiliser to approx. 0.037 KNU(S)/mL on the basis of their expected activity. The final dilution is made direct into the sample cup.

8. Procedure 8.1 Cobas Menu Program

The Cobas Menu Program is used to suggest the weight/dilutions of samples and level control to be used.

The samples are entered into the program with a unique identification code and a worklist is printed out The samples and control are weighed out and diluted as stated on the worklist with hand-written weight data is inserted into the BS-amylase analysis logbook The results are computered automatically by the Cobas Fara as described in item 9 and printed out along with the standard curve.

Worklists and results printouts are inserted into the BS-amylase analysis logbook.

8.2 Cobas Fara Set-up

The samples are placed in the sample rack

The five standards are placed in the calibration rack at position 1 to 5 (strongest standard at position 5), and control placed in the same rack at position 10.

The substrate is transferred to a 30 mL reagent container and placed in that reagent rack at position 2 (holder 1).

The α-glucosidase help reagent is transferred to a 50 mL reagent container and placed in the reagent rack at position 2 (holder C)

8.3 Cobas Fare Analysis

The main principles of the analysis are as follows: 20 μL sample and 10 μL rinse-water are pipetted into the cuvette along with 250 μL α-glucosidase help reagent. The cuvette rotates for 10 seconds and the reagents are thrown out into the horizontal cuvettes. 25 μL substrate and 20 μL rinse-water are pipetted off. After a 1 second wait to ensure that the temperature is 37° C., the cuvette rotates again and the substrate is mixed into the horizontal cuvettes. Absorbance is measured for the first time after 120 seconds and then every 5 seconds. Absorbance is measured a total of 37 times for each sample.

9. Calculations

The activity of the samples is calculated relative to Novo Nordisk A/S standard.

The standard curve is plotted by the analyzer. The curve is to be gently curved, rising steadily to an absorbance of around 0.25 for standard no. 5.

The activity of the samples in KNU(S)/mL is read off the standard curve by the analyzer.

The final calculations to allow for the weights/dilutions used employ the following formula:

Activity in KNU(S)/g=S×V×F/W

S=analysis result read off (KNU(S)/mL

V=volume of volumetric flask used in mL

F=dilution factor for second dilution

W=weight of enzyme sample in g 9.2 Calculation of Mean Values

Results are stated with 3 significant digits. However, for sample activity<10 KNU(S)/g, only 2 significant digits are given.

The following rules apply on calculation of mean values:

1. Data which deviates more than 2 standard deviations from the mean value is not included in the calculation.
2. Single and double determination over one run:

The mean value is calculated on basis of results lying within the standard curve's activity area.

3. Double determinations over two runs: All values are included in the mean value. Outliers are omitted.

10. Accuracy and Precision

The coefficient of variation is 2.9% based on retrospective validation of analysis results for a number of finished products and the level control.

Assay for α-Amylase Activity

α-Amylase activity is determined by a method employing Phadebas® tablets as substrate. Phadebas tablets (Phadebas® Amylase Test, supplied by Pharmacia Diagnostic) contain a cross-linked insoluble blue-coloured starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolysed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyse a certain amount of substrate and a blue colour will be produced. The colour intensity is measured at 620 nm. The measured absorbance is directly proportional to the specific activity (activity/mg of pure α-amylase protein) of the α-amylase in question under the given set of conditions.

EXAMPLES

Example 1

Construction of Variants of BSG α-amylase (SEQ ID NO: 3)

The gene encoding BSG, amyS, is located in plasmid pPL1117. This plasmid contains also the gene conferring resistance towards kanamycin and an origin of replication, both obtained from plasmid pUB110 (Gryczan, T. J. et al (1978) J.Bact 134:318–329).

The DNA sequence of the mature part of amys is shown as SEQ ID NO: 11 and the amino acid sequence of the mature protein is shown as SEQ ID NO: 3

BSG variant TVB145, which contains a deletion of 6 nucleotides corresponding to amino acids I181-G182 in the mature protein, is constructed as follows:

Polymerase Chain Reaction (PCR) is utilized to amplify the part of the amyS gene (from plasmid pPL1117), located between DNA primers BSG1 (SEQ ID NO: 15) and BSGM2 (SEQ ID NO: 18). BSG1 is identical to a part of the amyS gene whereas BSGM2 contains the 6 bp nucleotide deletion. A standard PCR reaction is carried out: 94° C. for 5 minutes, 25 cycles of (94° C. for 45 seconds, 50° C. for 45 seconds, 72° C. for 90 seconds), 72° C. for 7 minutes using the Pwo polymerase under conditions as recommended by the manufacturer, Boehringer Mannheim Gmbh.

The resulting approximately 550 bp amplified band was used as a megaprimer (Barik, S and Galinski, MS (1991): Biotechniques 10: 489–490) together with primer BSG3 in a second PCR with pPL1117 as template resulting in a DNA fragment of approximately 1080 bp.

This DNA fragment is digested with restriction endonucleases Acc65I and SalI and the resulting approximately 550 bp fragment is ligated into plasmid pPL1117 digested with the same enzymes and transformed into the protease- and amylase-deleted *Bacillus subtilis* strain SHA273 (described in WO92/11357 and WO95/10603). Kanamycin resistant and starch degrading transformants were analysed for the presence of the desired mutations (restriction digest to verify the introduction of a HindIII site in the gene). The DNA sequence between restriction sites Acc65I and SalI was verified by DNA sequencing to ensure the presence of only the desired mutations.

BSG variant TVB146 which contains the same 6 nucleotide deletion as TVB145 and an additional substitution of asparagine 193 for a phenylalanine, N193F, was constructed in a similar way as TVB145 utilizing primer BSGM3 (SEQ ID NO: 19) in the first PCR.

BSG variant TVB161, containing the deletion of I181-G182, N193F, and L204F, is constructed in a similar way as the two previous variants except that the template for the PCR reactions is plasmid pTVB146 (pPL1117 containing the TVB146-mutations within amyS and the mutagenic oligonucleotide for the first PCR is BSGM3.

BSG variant TVB162, containing the deletion of I181-G182, N193F, and E210H, is constructed in a similar way as TVB161 except that the mutagenic oligonucleotide is BSGM4 (SEQ ID NO: 20).

BSG variant TVB163, containing the deletion of I181-G182, N193F, and E214Q, is constructed in a similar way as TVB161 except that the mutagenic oligonucleotide is BSGM5 (SEQ ID NO: 21).

The above constructed BSG variants were then fermented and purified as described above in the "Material and Methods" section.

Example 2

Measurement of the Calcium- and pH-dependent Stability

Normally, the industrial liquefaction process runs using pH 6.0–6.2 as liquefaction pH and an addition of 40 ppm free calcium in order to improve the stability at 95° C.–105° C. Some of the herein proposed substitutions have been made in order to improve the stability at 1. lower pH than pH 6.2 and/or
2. at free calcium levels lower than 40 ppm free calcium.

Two different methods have been used to measure the improvements in stability obtained by the different substitutions in the α-amylase from *B.stearothermophilus:*

Method 1. One assay which measures the stability at reduced pH, pH 5.0, in the presence of 5 ppm free calcium. 10 μg of the variant were incubated under the following conditions: A 0.1 M acetate solution, pH adjusted to pH 5.0, containing 5 ppm calcium and 5% w/w common corn starch (free of calcium). Incubation was made in a water bath at 95° C. for 30 minutes.

Method 2. One assay which measure the stability in the absence of free calcium and where the pH is maintained at pH 6.0. This assay measures the decrease in calcium sensitivity: 10 μg of the variant were incubated under the following conditions: A 0.1 M acetate solution, pH adjusted to pH 6.0, containing 5% w/w common corn starch (free of calcium). Incubation was made in a water bath at 95° C. for 30 minutes.

Stability Determination

All the stability trials 1, 2 have been made using the same set up. The method was:

The enzyme was incubated under the relevant conditions (1–4). Samples were taken at 0, 5, 10, 15 and 30 minutes and diluted 25 times (same dilution for all taken samples) in assay buffer (0.1M 50 mM Britton buffer pH 7.3) and the activity was measured using the Phadebas assay (Pharmacia) under standard conditions pH 7.3, 37° C.

The activity measured before incubation (0 minutes) was used as reference (100%). The decline in percent was calculated as a function of the incubation time. The table shows the residual activity after 30 minutes of incubation.

Stability method 1. / Low pH stability improvement

| MINUTES OF INCUBATION | WT. SEQ. ID. NO: 3 AMYLASE (BSG) | SEQ. ID NO: 3 VARIANT WITH DELETION IN POS. I181-G182 (TVB145) | SEQ. ID NO: 3 VARIANT WITH DELETION IN POS. I181-G182 + N193F (TVB146) | SEQ. ID NO: 3 VARIANT WITH DELETION IN POS. I181-G182 + N193F + E214Q (TVB163) |
|---|---|---|---|---|
| 0 | 100 | 100 | 100 | 100 |
| 5 | 29 | 71 | 83 | 77 |
| 10 | 9 | 62 | 77 | 70 |
| 15 | 3 | 50 | 72 | 67 |
| 30 | 1 | 33 | 62 | 60 |

Stability Method 1./Low pH Stability Improvement

The temperature describet in method 1 has been reduced from 95° C. to 70° C. since the amylases mentioned for SEQ ID NO: 1 and 2 have a lower thermostability than the one for SEQ ID NO: 3.

| MINUTES OF INCUBATION | WT. SEQ. ID. NO: 2 AMYLASE | SEQ. ID NO: 2 VARIANT WITH DELETION IN POS. D183-G184 | SEQ. ID NO: 1 AMYLASE | SEQ. ID NO: 1 VARIANT WITH DELETION IN POS. T183-G184 |
|---|---|---|---|---|
| 0 | 100 | 100 | 100 | 100 |
| 5 | 73 | 92 | 41 | 76 |
| 10 | 59 | 88 | 19 | 69 |
| 15 | 48 | 91 | 11 | 62 |
| 30 | 28 | 92 | 3 | 59 |

Stability method 2. / Low calcium sensitivity

| MINUTES OF INCUBATION | WT. SEQ ID NO: 3 AMYLASE (BSG) | SEQ ID NO: 3 VARIANT WITH DELETION IN POS. I181-G182 (TVB145) | SEQ ID NO: 3 VARIANT WITH DELETION IN POS. I181-G182 + N193F (TVB146) | SEQ ID NO: 3 VARIANT WITH DELETION IN POS. I181-G182 + N193F + E214Q (TVB163) |
|---|---|---|---|---|
| 0 | 100 | 100 | 100 | 100 |
| 5 | 60 | 82 | 81 | 82 |
| 10 | 42 | 76 | 80 | 83 |
| 15 | 31 | 77 | 81 | 79 |
| 30 | 15 | 67 | 78 | 79 |

Specific Activity Determination.

The specific activity was determined using the Phadebas assay (Pharmacia) as activity/mg enzyme. The activity was determined using the α-amylase assay described in the Materials and Methods section herein.

The specific activity of the parent enzyme and a single and a double mutation was determined to:

BSG: SEQ ID NO:3 (Parent enzyme) 20000 NU/mg

TVB145: SEQ ID NO:3 with the deletion in positions I181-G182: (Single mutation) 34600 NU/mg TVB146: SEQ ID NO:3 with the deletion in positions I181-G182+N193F: (Double mutation) 36600 NU/mg TVB163: SEQ ID NO:3 with the deletion in positions I181-G182+N193F+E214Q: (Triple mutation) 36300 NU/mg Example 3

Pilot Plant Jet Cook and Liquefaction with Alpha-amylase Variant TVB146

Pilot plant liquefaction experiments were run in the mini-jet system using a dosage of 50 NU (S)/g DS at pH 5.5 with 5 ppm added $Ca^{++}$, to compare the performance of formulated BSG alpha-amylase variant TVB146 (SEQ ID NO: 3 with deletion in positions I181-G182+N193F) with that of parent BSG alpha-amylase (SEQ ID NO: 3). The reaction was monitored by measuring the DE increase (Neocuproine method) as a function of time.

Corn starch slurries were prepared by suspending 11.8 kg Cerestar C*Pharm GL 03406 (89 % starch) in deionized water and making up to 30 kg. The pH was adjusted to 5.5 at ambient temperature, after the addition of 0.55 g $CaCl_2 \cdot 2H_2O$.

The following enzymes were used:

| | |
|---|---|
| TVB146 | 108 KNU(S)/g, 146 KNU(SM9)/g |
| BSG amylase | 101 KNU(S)/g, 98 KNU(SM9)/g |

An amount of enzyme corresponding to 50 NU (SM9)/g DS was added, and the conductivity adjusted to 300 mS using NaCl. The standard conditions were as follows:

| | |
|---|---|
| Substrate concentration | 35% w/w (initial) |
| | 31.6–31.9% w/w (final) |
| Temperature | 105° C., 5 min (Primary liquefaction) |
| | 95° C., 90 min (Secondary liquefaction) |
| pH (initial) | 5.5 |

After jetting, the liquefied starch was collected and transported in sealed thermos-flasks from the pilot plant to the laboratory, where secondary liquefaction was continued at 95° C.

10 ml samples were taken at 15 minute intervals from 15–90 minutes. 2 drops of 1 N HCl were added to inactivate the enzyme. From these samples, 0.3–0.1 g (according to the expected DE) were weighed out and diluted to 100 ml. Reducing sugars were then determined according to the Neocuproine method (Determination of reducing sugar with improved precision. Dygert, Li, Florida and Thomas (1965). Anal. Biochem 13, 368) and DE values determined. The development of DE as a function of time is given in the following table:

| Time (min.) | TVB146 | BSG |
|---|---|---|
| | DE (neocuproine) | |
| 15 | 2.80 | 2.32 |
| 30 | 4.88 | 3.56 |
| 45 | 6.58 | 4.98 |
| 60 | 8.17 | 6.00 |
| 75 | 9.91 | 7.40 |
| 90 | 11.23 | 8.03 |

As can be seen the alpha-amylase variant TVB146 performed significantly better under industrially relevant application conditions at low levels of calcium than the parent BSG alpha-amylase.

Example 4

Jet Cook and Liquefaction with a Combination of Alpha-amylase Variants (TVB146 and LE174)

Jet cook and liquefaction using a combination of the alpha-amylase variants, TVB146 and LE174 (ratio 1:1) were carried out at the following conditions:

Substrate A.E. Staley food grade powdered corn starch (100 lbs)

D.S. 35% using DI water

Free $Ca^{2+}$ 2.7 ppm at pH 5.3 (none added, from the starch only)

Initial pH 5.3

Dose AF9 units (AF9 is available on request) for each enzyme variant was 28 NU/g starch db for a total dose of 56 NU/g Temperature in primary liquefaction 105° C.

Hold time in primary liquefaction 5 minutes

Temperature in secondary liquefaction 95° C.

At 15 minutes into secondary liquefaction 1.5 gms of hydrolyzate was added to a tared one liter volumetric containing 500 cc of DI water and 1 ml of one normal HCl and the 30 exact wt. added was recorded. This was repeated at 15 minute intervals out to 90 minutes with an additional point at 127 minutes. These were diluted to one liter and determined for dextrose equivalence via Neocuproine method as discribed by Dygert, Li, Florida and Thomas. Determination of reducing sugar with improved precision (1965). Anal. Biochem 13, 368.

The results were as follows:

| Time | DE |
|---|---|
| 15 | 3.2 |
| 30 | 4.8 |
| 45 | 6.3 |
| 60 | 7.8 |
| 75 | 9.4 |
| 90 | 10.4 |
| 127 | 13.1 |

REFERENCES CITED

Klein, C., et al., *Biochemistry* 1992, 31, 8740–8746.

Mizuno, H., et al., *J. Mol. Biol.* (1993) 234, 1282–1283.

Chang, C., et al, *J. Mol. Biol.* (1993) 229, 235–238.

Larson, S. B., *J. Mol. Biol.* (1994) 235, 1560–1584.

Lawson, C. L., *J. Mol. Biol.* (1994) 236, 590–600.

Qian, M., et al., *J. Mol. Biol.* (1993) 231, 785–799.

Brady, R. L., et al., *Acta Crystallogr. sect. B*, 47, 527–535.

Swift, H. J., et al., *Acta Crystallogr. sect. B*, 47, 535–544.

A. Kadziola, Ph.D. Thesis: "An alpha-amylase from Barley and its Complex with a Substrate Analogue Inhibitor Studied by X-ray Crystallography", Department of Chemistry University of Copenhagen 1993.

MacGregor, E. A., *Food Hydrocolloids*, 1987, Vol.1, No. 5–6.

B. Diderichsen and L. Christiansen, Cloning of a maltogenic α-amylase from *Bacillus stearothermophilus*, FEMS Microbiol. letters: 56: pp. 53–60 (1988).

Hudson et al., Practical Immunology, Third edition (1989), Blackwell Scientific Publications.

Sambrook et al., *Molecular Cloning: A Laboratory Manual*, 2nd Ed., Cold Spring Harbor, 1989.

S. L. Beaucage and M. H. Caruthers, *Tetrahedron Letters* 22, 1981, pp. 1859–1869

Matthes et al., *The EMBO J.* 3, 1984, pp. 801–805.

R. K. Saiki et al., *Science* 239, 1988, pp. 487–491.

Morinaga et al., (1984, Biotechnology 2:646–639)

Nelson and Long, *Analytical Biochemistry* 180, 1989, pp. 147–151

Hunkapiller et al., 1984, Nature 310:105–111

R. Higuchi, B. Krummel, and R. K. Saiki (1988). A general method of in vitro preparation and specific mutagenesis of DNA fragments: study of protein and DNA interactions. *Nucl. Acids Res.* 16:7351–7367.

Dubnau et al., 1971, *J. Mol. Biol.* 56, pp. 209–221.

Gryczan et al., 1978, *J. Bacteriol.* 134, pp. 318–329.

S. D. Erlich, 1977, *Proc. Natl. Acad. Sci.* 74, pp. 1680–1682.

Boel et al., 1990, *Biochemistry* 29, pp. 6244–6249.

What is claimed is:

1. A polypeptide having α-amylase activity comprising a polypeptide having at least two alterations relative to a parent α-amylase, wherein A) In SEQ ID NO:1, at least one of said alterations is selected from the group consisting of R181*, G182*, T183*, and G184*; and at least one of said alterations is selected from the group consisting of N195A,R,D,C,E,Q,G,H,I,L,K,M,F,P,S,T,W,Y, and V;

B) In SEQ ID NO:2, at least one of said alterations is selected from the group consisting of R181*, G182*, D183*, and G184* and at least one of said alterations is selected from the group consisting of N195A,R,D,C,E,Q,G,H,I,L,K,M,F,P,S,T,W,Y, and V;

C) In SEQ ID NO:3, at least one of said alterations is selected from the group consisting of R179*, G180, I181*, and G182* and at least one of said alterations is selected from the group consisting of N193A,R,D,C,E,Q,G,H,I,L,K,M,F,P,S,T,W,Y,V;

D) In SEQ ID NO:4, at least one of said alterations is selected from the group consisting of Q178* and G179* and at least one of said alterations is selected from the group consisting of N190A,R,D,C,E,Q,G,H,I,L,K,M,F,P,S,T,W,Y, and V;

E) In SEQ ID NO:5, at least one of said alterations is selected from the group consisting of R176*, G177*, E178, G179* and at least one of said alterations is selected from the group consisting of N190A,R,D,C,E,Q,G,H,I,L,K,M,F,P,S,T,W,Y, and V;

E) In SEQ ID NO:6, at least one of said alterations is selected from the group consisting of R181*, G182*, H183*, and G184* and at least one of said alterations is selected from the group consisting of N195A,R,D,C,E,Q,G,H,I,L,K,M,F,P,S,T,W,Y, and V; and G) in an α-amylase polypeptide having at least 60% homology to any of SEQ ID NO:s 1–6 or combinations thereof, (i) at least one of said alterations is a deletion of a residue corresponding to R181, G182, T183, or G184 of SEQ ID NO:1; R181, G182, T183, or G184 of SEQ ID NO:2; R179, G180, I181, or G182 of SEQ ID NO:3; Q178 or G179 in SEQ ID NO:4; R176, G177, E178, or G179 in SEQ ID NO:5; or R181, G182, H183, or G184 in SEQ ID NO:6 and (ii) at least one of said alterations is a substitution of a residue corresponding to N195 in SEQ ID Nos: 1, 2, or 6; N193 in SEQ ID NO:3; or N190 in SEQ ID NOs:4 or 5 with an amino acid selected from the group consisting of A,R,D,C,E,Q,G,H,I,L,K,M,F,P, S,T,W,Y, and V.

2. A polypeptide as defined in claim 1, wherein said alterations comprise I181*, G182*, and N193F in SEQ ID NO: 3 or in corresponding positions in another parent α-amylase.

3. A polypeptide as defined in claim 2, wherein said alterations further comprise a substitution in position E214Q in SEQ ID NO: 3 or in a corresponding position in another parent α-amylase.

4. A polypeptide as defined in claim 1, wherein the parent α-amylase is a hybrid αmamylase of SEQ ID NO: 4 and SEQ ID NO: 5.

5. A polypeptide as defined in claim 4, wherein the parent hybrid alpha-amylase comprises the 445 C-termiinal amino acid residues of the *B. licheniformis* α-amylase shown in SEQ ID NO: 4 and the 37 N-terminal amino acid residues of the α-amylase derived from *B. amyloliquefaciens* shown in SEQ ID NO: 5.

6. A polypeptide as defined in claim 5, wherein the parent hybrid further comprises: H156Y+A181T+N190F+A209V+Q264S (using the numbering in SEQ ID NO: 4).

7. A polypeptide as defined in claim 1, wherein said at least one alteration results in increased stability at acidic pH and/or at low $Ca^{2+}$ concentration relative to the parent α-amylase.

8. A detergent additive comprising a polypeptide as defined in claim 1.

9. A detergent additive according to claim 8 comprising 0.02–200 mg of enzyme protein/g of the additive.

10. A detergent additive according to claim 8, further comprising an enzyme selected from the group consisting of a protease, a lipase, a peroxidase, another amylolytic enzyme, a cellulase, and combinations of any of the foregoing.

11. A detergent composition comprising a polypeptide as defined in claim 1.

12. The detergent composition according to claim 11 further comprising an enzyme selected from the group consisting of a protease, a lipase, a peroxidase, another amylolytic enzyme, a cellulase, and combinations of any of the foregoing.

13. A manual or automatic dishwashing detergent composition comprising a polypeptide as defined in claim 1.

14. A dishwashing detergent composition according to claim 13 further comprising an enzyme selected from the group consisting of a protease, a lipase, a peroxidase, another amylolytic enzyme, a cellulase, and combinations of any of the foregoing.

15. A manual or automatic laundry washing composition comprising a polypeptide as defined in claim 1.

16. A laundry washing composition according to claim 15 further comprising an enzyme selected from the goup consisting of a protease, a lipase, a peroxidase, an amylolytic enzyme, a cellulase, and combinations of any of the foregoing.

17. A composition comprising a mixture selected from the group consisting of:

(i) a mixture of the α-amylase from *B. licheniformis* having the sequence shown in SEQ ID NO: 4 with one or more polypeptides as defined in claim 1, wherein said polypeptides are derived from a parent α-amylase having the sequence shown in SEQ ID NO: 3;

(ii) a mixture of the α-amylase from *B. stearothermophilus* having the sequence shown in SEQ ID NO: 3 with one or more polypeptides as defined in claim 1, wherein said polypeptides are derived from one or more other parent Termamyl-like α-amylases; and (iii) a mixture of one or more polypeptides as defined in claim 1 derived from a parent α-amylase having the sequence shown in SEQ ID NO: 3 with one or more polypeptides as defined in claim 1 derived from a different parent α-amylase.

18. A composition comprising:

a mixture of (i) one or more polypeptides as defined in claim 1 derived from a parent α-amylase having the sequence shown in SEQ ID NO: 3 and (ii) one or more polypeptides as defined in claim 1 derived from a parent α-amylase having the sequence shown in SEQ ID NO: 4.

19. A composition comprising:

a mixture of (i) one or more polypeptides as defined in claim 1 derived from a parent α-amylase having the sequence shown in SEQ ID NO: 3 and (ii) a hybrid α-amylase comprising a part of the *B. amyloliquefaciens* α-amylase shown in SEQ ID NO: 5 and a part of the *B. licheniformis* α-amylase shown in SEQ ID NO: 4.

20. The composition according to claim 19, wherein the hybrid α-amylase is a hybrid α-amylase comprising the 445 C-terminal amino acid residues of the *B. licheniformis* α-amylase shown in SEQ ID NO: 4 and the 37 N-terminal amino acid residues of the α-amylase derived from *B. amyloliquefaciens* shown in SEQ ID NO: 5.

21. The composition according to claim 20, wherein the hybrid α-amylase further comprises the following alterations relative to SEQ ID NO:4: H156Y+A181T+N190F+A209V+Q264S.

22. The composition according to claim 19, comprising a mixture of TVB146 and LE174.

* * * * *

SEQUENCE LISTING

```
<160> NUMBER OF SEQ ID NOS: 22

<210> SEQ ID NO 1
<211> LENGTH: 485
<212> TYPE: PRT
<213> ORGANISM: Bacillus sp.

<400> SEQUENCE: 1

His His Asn Gly Thr Asn Gly Thr Met Met Gln Tyr Phe Glu Trp Tyr
 1               5                  10                  15
Leu Pro Asn Asp Gly Asn His Trp Asn Arg Leu Arg Asp Asp Ala Ala
            20                  25                  30
Asn Leu Lys Ser Lys Gly Ile Thr Ala Val Trp Ile Pro Pro Ala Trp
        35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Asn Gln Leu Gln Ala Ala Val Thr Ser Leu Lys Asn Asn Gly
                85                  90                  95
Ile Gln Val Tyr Gly Asp Val Val Met Asn His Lys Gly Gly Ala Asp
            100                 105                 110
Gly Thr Glu Ile Val Asn Ala Val Glu Val Asn Arg Ser Asn Arg Asn
        115                 120                 125
Gln Glu Thr Ser Gly Glu Tyr Ala Ile Glu Ala Trp Thr Lys Phe Asp
    130                 135                 140
Phe Pro Gly Arg Gly Asn Asn His Ser Ser Phe Lys Trp Arg Trp Tyr
145                 150                 155                 160
His Phe Asp Gly Thr Asp Trp Asp Gln Ser Arg Gln Leu Gln Asn Lys
                165                 170                 175
Ile Tyr Lys Phe Arg Gly Thr Gly Lys Ala Trp Asp Trp Glu Val Asp
            180                 185                 190
Thr Glu Asn Gly Asn Tyr Asp Tyr Leu Met Tyr Ala Asp Val Asp Met
        195                 200                 205
Asp His Pro Glu Val Ile His Glu Leu Arg Asn Trp Gly Val Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Pro Met Phe Ala Val Ala Glu Phe Trp Lys Asn Asp Leu
            260                 265                 270
Gly Ala Ile Glu Asn Tyr Leu Asn Lys Thr Ser Trp Asn His Ser Val
        275                 280                 285
Phe Asp Val Pro Leu His Tyr Asn Leu Tyr Asn Ala Ser Asn Ser Gly
    290                 295                 300
Gly Tyr Tyr Asp Met Arg Asn Ile Leu Asn Gly Ser Val Val Gln Lys
305                 310                 315                 320
His Pro Thr His Ala Val Thr Phe Val Asp Asn His Asp Ser Gln Pro
                325                 330                 335
Gly Glu Ala Leu Glu Ser Phe Val Gln Gln Trp Phe Lys Pro Leu Ala
            340                 345                 350
Tyr Ala Leu Val Leu Thr Arg Glu Gln Gly Tyr Pro Ser Val Phe Tyr
        355                 360                 365
Gly Asp Tyr Tyr Gly Ile Pro Thr His Gly Val Pro Ala Met Lys Ser
    370                 375                 380
Lys Ile Asp Pro Leu Leu Gln Ala Arg Gln Thr Phe Ala Tyr Gly Thr
385                 390                 395                 400
Gln His Asp Tyr Phe Asp His His Asp Ile Ile Gly Trp Thr Arg Glu
                405                 410                 415
Gly Asn Ser Ser His Pro Asn Ser Gly Leu Ala Thr Ile Met Ser Asp
            420                 425                 430
Gly Pro Gly Gly Asn Lys Trp Met Tyr Val Gly Lys Asn Lys Ala Gly
        435                 440                 445
```

-continued

```
Gln Val Trp Arg Asp Ile Thr Gly Asn Arg Thr Gly Thr Val Thr Ile
    450                 455                 460
Asn Ala Asp Gly Trp Gly Asn Phe Ser Val Asn Gly Gly Ser Val Ser
465                 470                 475                 480
Val Trp Val Lys Gln
                485
```

<210> SEQ ID NO 2
<211> LENGTH: 485
<212> TYPE: PRT
<213> ORGANISM: Bacillus sp.

<400> SEQUENCE: 2

```
His His Asn Gly Thr Asn Gly Thr Met Met Gln Tyr Phe Glu Trp His
 1               5                  10                  15
Leu Pro Asn Asp Gly Asn His Trp Asn Arg Leu Arg Asp Asp Ala Ser
            20                  25                  30
Asn Leu Arg Asn Arg Gly Ile Thr Ala Ile Trp Ile Pro Pro Ala Trp
        35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Glu Ser Ala Ile His Ala Leu Lys Asn Asn Gly
                85                  90                  95
Val Gln Val Tyr Gly Asp Val Val Met Asn His Lys Gly Gly Ala Asp
            100                 105                 110
Ala Thr Glu Asn Val Leu Ala Val Glu Val Asn Pro Asn Asn Arg Asn
        115                 120                 125
Gln Glu Ile Ser Gly Asp Tyr Thr Ile Glu Ala Trp Thr Lys Phe Asp
    130                 135                 140
Phe Pro Gly Arg Gly Asn Thr Tyr Ser Asp Phe Lys Trp Arg Trp Tyr
145                 150                 155                 160
His Phe Asp Gly Val Asp Trp Asp Gln Ser Arg Gln Phe Gln Asn Arg
                165                 170                 175
Ile Tyr Lys Phe Arg Gly Asp Gly Lys Ala Trp Asp Trp Glu Val Asp
            180                 185                 190
Ser Glu Asn Gly Asn Tyr Asp Tyr Leu Met Tyr Ala Asp Val Asp Met
        195                 200                 205
Asp His Pro Glu Val Val Asn Glu Leu Arg Arg Trp Gly Glu Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Ala
                245                 250                 255
Thr Gly Lys Glu Met Phe Ala Val Ala Glu Phe Trp Lys Asn Asp Leu
            260                 265                 270
Gly Ala Leu Glu Asn Tyr Leu Asn Lys Thr Asn Trp Asn His Ser Val
        275                 280                 285
Phe Asp Val Pro Leu His Tyr Asn Leu Tyr Asn Ala Ser Asn Ser Gly
    290                 295                 300
Gly Asn Tyr Asp Met Ala Lys Leu Leu Asn Gly Thr Val Val Gln Lys
305                 310                 315                 320
His Pro Met His Ala Val Thr Phe Val Asp Asn His Asp Ser Gln Pro
                325                 330                 335
Gly Glu Ser Leu Glu Ser Phe Val Gln Glu Trp Phe Lys Pro Leu Ala
            340                 345                 350
Tyr Ala Leu Ile Leu Thr Arg Glu Gln Gly Tyr Pro Ser Val Phe Tyr
        355                 360                 365
Gly Asp Tyr Tyr Gly Ile Pro Thr His Ser Val Pro Ala Met Lys Ala
    370                 375                 380
Lys Ile Asp Pro Ile Leu Glu Ala Arg Gln Asn Phe Ala Tyr Gly Thr
385                 390                 395                 400
Gln His Asp Tyr Phe Asp His His Asn Ile Ile Gly Trp Thr Arg Glu
                405                 410                 415
Gly Asn Thr Thr His Pro Asn Ser Gly Leu Ala Thr Ile Met Ser Asp
            420                 425                 430
Gly Pro Gly Gly Glu Lys Trp Met Tyr Val Gly Gln Asn Lys Ala Gly
        435                 440                 445
Gln Val Trp His Asp Ile Thr Gly Asn Lys Pro Gly Thr Val Thr Ile
    450                 455                 460
Asn Ala Asp Gly Trp Ala Asn Phe Ser Val Asn Gly Gly Ser Val Ser
465                 470                 475                 480
Ile Trp Val Lys Arg
                485
```

-continued

<210> SEQ ID NO 3
<211> LENGTH: 514
<212> TYPE: PRT
<213> ORGANISM: B. stearothermophilus

<400> SEQUENCE: 3

```
Ala Ala Pro Phe Asn Gly Thr Met Met Gln Tyr Phe Glu Trp Tyr Leu
 1               5                  10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Ala Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Ser Trp Gly Lys Trp Tyr Val Asn
    210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Asp Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Met Lys Thr Asn Gly Thr Met Ser Leu Phe Asp
        275                 280                 285
Ala Pro Leu His Asn Lys Phe Tyr Thr Ala Ser Lys Ser Gly Gly Thr
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
Phe Tyr Asp Leu Thr Gly Asn Arg Ser Asp Thr Val Thr Ile Asn Ser
    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Trp Ser Ile Thr Thr
                485                 490                 495
Arg Pro Trp Thr Asp Glu Phe Val Arg Trp Thr Glu Pro Arg Leu Val
            500                 505                 510
Ala Trp
```

<210> SEQ ID NO 4
<211> LENGTH: 483
<212> TYPE: PRT
<213> ORGANISM: B. licheniformis -continued

<400> SEQUENCE: 4

```
Ala Asn Leu Asn Gly Thr Leu Met Gln Tyr Phe Glu Trp Tyr Met Pro
 1               5                  10                  15
Asn Asp Gly Gln His Trp Arg Arg Leu Gln Asn Asp Ser Ala Tyr Leu
            20                  25                  30
Ala Glu His Gly Ile Thr Ala Val Trp Ile Pro Pro Ala Tyr Lys Gly
        35                  40                  45
Thr Ser Gln Ala Asp Val Gly Tyr Gly Ala Tyr Asp Leu Tyr Asp Leu
    50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
        115                 120                 125
Ile Ser Gly Glu His Leu Ile Lys Ala Trp Thr His Phe His Phe Pro
    130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
            180                 185                 190
Tyr Asp Tyr Leu Met Tyr Ala Asp Ile Asp Tyr Asp His Pro Asp Val
        195                 200                 205
Ala Ala Glu Ile Lys Arg Trp Gly Thr Trp Tyr Ala Asn Glu Leu Gln
    210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Gly Tyr Asp Met
    290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
        435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480
Val Gln Arg
```

<210> SEQ ID NO 5
<211> LENGTH: 480
<212> TYPE: PRT
<213> ORGANISM: B. amyloliquefaciens

<400> SEQUENCE: 5

```
Val Asn Gly Thr Leu Met Gln Tyr Phe Glu Trp Tyr Thr Pro Asn Asp
 1               5                  10                  15
Gly Gln His Trp Lys Arg Leu Gln Asn Asp Ala Glu His Leu Ser Asp
            20                  25                  30
Ile Gly Ile Thr Ala Val Trp Ile Pro Pro Ala Tyr Lys Gly Leu Ser
        35                  40                  45
Gln Ser Asp Asn Gly Tyr Gly Pro Tyr Asp Leu Tyr Asp Leu Gly Glu
```

-continued

```
    50                  55                  60
Phe Gln Gln Lys Gly Thr Val Arg Thr Lys Tyr Gly Thr Lys Ser Glu
65                  70                  75                  80
Leu Gln Asp Ala Ile Gly Ser Leu His Ser Arg Asn Val Gln Val Tyr
                85                  90                  95
Gly Asp Val Val Leu Asn His Lys Ala Gly Ala Asp Ala Thr Glu Asp
            100                 105                 110
Val Thr Ala Val Glu Val Asn Pro Ala Asn Arg Asn Gln Glu Thr Ser
        115                 120                 125
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
Tyr Asp Tyr Leu Met Tyr Ala Asp Val Asp Tyr Asp His Pro Asp Val
        195                 200                 205
Val Ala Glu Thr Lys Lys Trp Gly Ile Trp Tyr Ala Asn Glu Leu Ser
    210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
        275                 280                 285
His Phe Asn Leu Gln Ala Ala Ser Ser Gln Gly Gly Gly Tyr Asp Met
    290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Thr Ser Pro Lys Glu Ile Pro Ser Leu Lys Asp Asn Ile
    370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
                405                 410                 415
Ser Ser Ala Ala Lys Ser Gly Leu Ala Ala Leu Ile Thr Asp Gly Pro
            420                 425                 430
Gly Gly Ser Lys Arg Met Tyr Ala Gly Leu Lys Asn Ala Gly Glu Thr
        435                 440                 445
Trp Tyr Asp Ile Thr Gly Asn Arg Ser Asp Thr Val Lys Ile Gly Ser
    450                 455                 460
Asp Gly Trp Gly Glu Phe His Val Asn Asp Gly Ser Val Ser Ile Tyr
465                 470                 475                 480
```

<210> SEQ ID NO 6
<211> LENGTH: 485
<212> TYPE: PRT
<213> ORGANISM: Bacillus sp.

<400> SEQUENCE: 6

```
His His Asn Gly Thr Asn Gly Thr Met Met Gln Tyr Phe Glu Trp Tyr
 1               5                  10                  15
Leu Pro Asn Asp Gly Asn His Trp Asn Arg Leu Asn Ser Asp Ala Ser
            20                  25                  30
Asn Leu Lys Ser Lys Gly Ile Thr Ala Val Trp Ile Pro Pro Ala Trp
        35                  40                  45
Lys Gly Ala Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Gln Ala Ala Val Thr Ser Leu Lys Asn Asn Gly
                85                  90                  95
Ile Gln Val Tyr Gly Asp Val Val Met Asn His Lys Gly Gly Ala Asp
            100                 105                 110
Ala Thr Glu Met Val Arg Ala Val Glu Val Asn Pro Asn Asn Arg Asn
        115                 120                 125
Gln Glu Val Thr Gly Glu Tyr Thr Ile Glu Ala Trp Thr Arg Phe Asp
```

-continued

```
        130                 135                 140
    Phe Pro Gly Arg Gly Asn Thr His Ser Ser Phe Lys Trp Arg Trp Tyr
    145                 150                 155                 160
    His Phe Asp Gly Val Asp Trp Asp Gln Ser Arg Arg Leu Asn Asn Arg
                    165                 170                 175
    Ile Tyr Lys Phe Arg Gly His Gly Lys Ala Trp Asp Trp Glu Val Asp
                180                 185                 190
    Thr Glu Asn Gly Asn Tyr Asp Tyr Leu Met Tyr Ala Asp Ile Asp Met
            195                 200                 205
    Asp His Pro Glu Val Val Asn Glu Leu Arg Asn Trp Gly Val Trp Tyr
        210                 215                 220
    Thr Asn Thr Leu Gly Leu Asp Gly Phe Arg Ile Asp Ala Val Lys His
    225                 230                 235                 240
    Ile Lys Tyr Ser Phe Thr Arg Asp Trp Ile Asn His Val Arg Ser Ala
                    245                 250                 255
    Thr Gly Lys Asn Met Phe Ala Val Ala Glu Phe Trp Lys Asn Asp Leu
                260                 265                 270
    Gly Ala Ile Glu Asn Tyr Leu Gln Lys Thr Asn Trp Asn His Ser Val
            275                 280                 285
    Phe Asp Val Pro Leu His Tyr Asn Leu Tyr Asn Ala Ser Lys Ser Gly
        290                 295                 300
    Gly Asn Tyr Asp Met Arg Asn Ile Phe Asn Gly Thr Val Val Gln Arg
    305                 310                 315                 320
    His Pro Ser His Ala Val Thr Phe Val Asp Asn His Asp Ser Gln Pro
                    325                 330                 335
    Glu Glu Ala Leu Glu Ser Phe Val Glu Glu Trp Phe Lys Pro Leu Ala
                340                 345                 350
    Tyr Ala Leu Thr Leu Thr Arg Glu Gln Gly Tyr Pro Ser Val Phe Tyr
            355                 360                 365
    Gly Asp Tyr Tyr Gly Ile Pro Thr His Gly Val Pro Ala Met Arg Ser
        370                 375                 380
    Lys Ile Asp Pro Ile Leu Glu Ala Arg Gln Lys Tyr Ala Tyr Gly Lys
    385                 390                 395                 400
    Gln Asn Asp Tyr Leu Asp His His Asn Ile Ile Gly Trp Thr Arg Glu
                    405                 410                 415
    Gly Asn Thr Ala His Pro Asn Ser Gly Leu Ala Thr Ile Met Ser Asp
                420                 425                 430
    Gly Ala Gly Gly Ser Lys Trp Met Phe Val Gly Arg Asn Lys Ala Gly
            435                 440                 445
    Gln Val Trp Ser Asp Ile Thr Gly Asn Arg Thr Gly Thr Val Thr Ile
        450                 455                 460
    Asn Ala Asp Gly Trp Gly Asn Phe Ser Val Asn Gly Gly Ser Val Ser
    465                 470                 475                 480
    Ile Trp Val Asn Lys
                    485
```

<210> SEQ ID NO 7
<211> LENGTH: 485
<212> TYPE: PRT
<213> ORGANISM: Bacillus sp.

<400> SEQUENCE: 7

```
    His His Asn Gly Thr Asn Gly Thr Met Met Gln Tyr Phe Glu Trp Tyr
     1               5                  10                  15
    Leu Pro Asn Asp Gly Asn His Trp Asn Arg Leu Arg Asp Asp Ala Ala
                20                  25                  30
    Asn Leu Lys Ser Lys Gly Ile Thr Ala Val Trp Ile Pro Pro Ala Trp
            35                  40                  45
    Lys Gly Thr Ser Gln Asn Asp Val Gly Tyr Gly Ala Tyr Asp Leu Tyr
        50                  55                  60
    Asp Leu Gly Glu Phe Asn Gln Lys Gly Thr Val Arg Thr Lys Tyr Gly
    65                  70                  75                  80
    Thr Arg Asn Gln Leu Gln Ala Ala Val Thr Ser Leu Lys Asn Asn Gly
                    85                  90                  95
    Ile Gln Val Tyr Gly Asp Val Val Met Asn His Lys Gly Gly Ala Asp
                100                 105                 110
    Gly Thr Glu Ile Val Asn Ala Val Glu Val Asn Arg Ser Asn Arg Asn
            115                 120                 125
    Gln Glu Thr Ser Gly Glu Tyr Ala Ile Glu Ala Trp Thr Lys Phe Asp
        130                 135                 140
    Phe Pro Gly Arg Gly Asn Asn His Ser Ser Phe Lys Trp Arg Trp Tyr
    145                 150                 155                 160
    His Phe Asp Gly Thr Asp Trp Asp Gln Ser Arg Gln Leu Gln Asn Lys
                    165                 170                 175
    Ile Tyr Lys Phe Arg Gly Thr Gly Lys Ala Trp Asp Trp Glu Val Asp
                180                 185                 190
    Thr Glu Asn Gly Asn Tyr Asp Tyr Leu Met Tyr Ala Asp Val Asp Met
```

-continued

```
        195                 200                 205
Asp His Pro Glu Val Ile His Glu Leu Arg Asn Trp Gly Val Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Pro Met Phe Ala Val Ala Glu Phe Trp Lys Asn Asp Leu
            260                 265                 270
Gly Ala Ile Glu Asn Tyr Leu Asn Lys Thr Ser Trp Asn His Ser Val
        275                 280                 285
Phe Asp Val Pro Leu His Tyr Asn Leu Tyr Asn Ala Ser Asn Ser Gly
    290                 295                 300
Gly Tyr Tyr Asp Met Arg Asn Ile Leu Asn Gly Ser Val Val Gln Lys
305                 310                 315                 320
His Pro Thr His Ala Val Thr Phe Val Asp Asn His Asp Ser Gln Pro
                325                 330                 335
Gly Glu Ala Leu Glu Ser Phe Val Gln Gln Trp Phe Lys Pro Leu Ala
            340                 345                 350
Tyr Ala Leu Val Leu Thr Arg Glu Gln Gly Tyr Pro Ser Val Phe Tyr
        355                 360                 365
Gly Asp Tyr Tyr Gly Ile Pro Thr His Gly Val Pro Ala Met Lys Ser
    370                 375                 380
Lys Ile Asp Pro Leu Leu Gln Ala Arg Gln Thr Phe Ala Tyr Gly Thr
385                 390                 395                 400
Gln His Asp Tyr Phe Asp His His Asp Ile Ile Gly Trp Thr Arg Glu
                405                 410                 415
Gly Asn Ser Ser His Pro Asn Ser Gly Leu Ala Thr Ile Met Ser Asp
            420                 425                 430
Gly Pro Gly Gly Asn Lys Trp Met Tyr Val Gly Lys Asn Lys Ala Gly
        435                 440                 445
Gln Val Trp Arg Asp Ile Thr Gly Asn Arg Thr Gly Thr Val Thr Ile
    450                 455                 460
Asn Ala Asp Gly Trp Gly Asn Phe Ser Val Asn Gly Gly Ser Val Ser
465                 470                 475                 480
Val Trp Val Lys Gln
                485
```

<210> SEQ ID NO 8
<211> LENGTH: 485
<212> TYPE: PRT
<213> ORGANISM: Bacillus sp.

<400> SEQUENCE: 8

```
His His Asn Gly Thr Asn Gly Thr Met Met Gln Tyr Phe Glu Trp His
 1               5                  10                  15
Leu Pro Asn Asp Gly Asn His Trp Asn Arg Leu Arg Asp Asp Ala Ser
            20                  25                  30
Asn Leu Arg Asn Arg Gly Ile Thr Ala Ile Trp Ile Pro Pro Ala Trp
        35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Glu Ser Ala Ile His Ala Leu Lys Asn Asn Gly
                85                  90                  95
Val Gln Val Tyr Gly Asp Val Val Met Asn His Lys Gly Gly Ala Asp
            100                 105                 110
Ala Thr Glu Asn Val Leu Ala Val Glu Val Asn Pro Asn Asn Arg Asn
        115                 120                 125
Gln Glu Ile Ser Gly Asp Tyr Thr Ile Glu Ala Trp Thr Lys Phe Asp
    130                 135                 140
Phe Pro Gly Arg Gly Asn Thr Tyr Ser Asp Phe Lys Trp Arg Trp Tyr
145                 150                 155                 160
His Phe Asp Gly Val Asp Trp Asp Gln Ser Arg Gln Phe Gln Asn Arg
                165                 170                 175
Ile Tyr Lys Phe Arg Gly Asp Gly Lys Ala Trp Asp Trp Glu Val Asp
            180                 185                 190
Ser Glu Asn Gly Asn Tyr Asp Tyr Leu Met Tyr Ala Asp Val Asp Met
        195                 200                 205
Asp His Pro Glu Val Val Asn Glu Leu Arg Arg Trp Gly Glu Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Ala
                245                 250                 255
Thr Gly Lys Glu Met Phe Ala Val Ala Glu Phe Trp Lys Asn Asp Leu
```

-continued

```
            260                 265                 270
Gly Ala Leu Glu Asn Tyr Leu Asn Lys Thr Asn Trp Asn His Ser Val
        275                 280                 285
Phe Asp Val Pro Leu His Tyr Asn Leu Tyr Asn Ala Ser Asn Ser Gly
    290                 295                 300
Gly Asn Tyr Asp Met Ala Lys Leu Leu Asn Gly Thr Val Val Gln Lys
305                 310                 315                 320
His Pro Met His Ala Val Thr Phe Val Asp Asn His Asp Ser Gln Pro
                325                 330                 335
Gly Glu Ser Leu Glu Ser Phe Val Gln Glu Trp Phe Lys Pro Leu Ala
            340                 345                 350
Tyr Ala Leu Ile Leu Thr Arg Glu Gln Gly Tyr Pro Ser Val Phe Tyr
        355                 360                 365
Gly Asp Tyr Tyr Gly Ile Pro Thr His Ser Val Pro Ala Met Lys Ala
    370                 375                 380
Lys Ile Asp Pro Ile Leu Glu Ala Arg Gln Asn Phe Ala Tyr Gly Thr
385                 390                 395                 400
Gln His Asp Tyr Phe Asp His His Asn Ile Ile Gly Trp Thr Arg Glu
                405                 410                 415
Gly Asn Thr Thr His Pro Asn Ser Gly Leu Ala Thr Ile Met Ser Asp
            420                 425                 430
Gly Pro Gly Gly Glu Lys Trp Met Tyr Val Gly Gln Asn Lys Ala Gly
        435                 440                 445
Gln Val Trp His Asp Ile Thr Gly Asn Lys Pro Gly Thr Val Thr Ile
    450                 455                 460
Asn Ala Asp Gly Trp Ala Asn Phe Ser Val Asn Gly Gly Ser Val Ser
465                 470                 475                 480
Ile Trp Val Lys Arg
                485
```

<210> SEQ ID NO 9
<211> LENGTH: 1455
<212> TYPE: DNA
<213> ORGANISM: Bacillus sp.

<400> SEQUENCE: 9

```
catcataatg gaacaaatgg tactatgatg caatatttcg aatggtattt gccaaatgac      60
gggaatcatt ggaacaggtt gagggatgac gcagctaact taaagagtaa agggataaca     120
gctgtatgga tcccacctgc atggaagggg acttcccaga atgatgtagg ttatggagcc     180
tatgatttat atgatcttgg agagtttaac cagaagggga cggttcgtac aaaatatgga     240
acacgcaacc agctacaggc tgcggtgacc tctttaaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420
acaaagtttg attttcctgg aagaggaaat aaccattcca gctttaagtg gcgctggtat     480
cattttgatg ggacagattg ggatcagtca cgccagcttc aaaacaaaat atataaattc     540
aggggaacag gcaaggcctg ggactgggaa gtcgatacag agaatggcaa ctatgactat     600
cttatgtatg cagacgtgga tatggatcac ccagaagtaa tacatgaact tagaaactgg     660
ggagtgtggt atacgaatac actgaacctt gatggattta gaatagatgc agtgaaacat     720
ataaaatata gctttacgag agattggctt acacatgtgc gtaacaccac aggtaaacca     780
atgtttgcag tggctgagtt ttggaaaaat gaccttggtg caattgaaaa ctatttgaat     840
aaaacaagtt ggaatcactc ggtgtttgat gttcctctcc actataattt gtacaatgca     900
tctaatagcg gtggttatta tgatatgaga aatattttaa atggttctgt ggtgcaaaaa     960
catccaacac atgccgttac ttttgttgat aaccatgatt ctcagcccgg ggaagcattg    1020
gaatcctttg ttcaacaatg gtttaaacca cttgcatatg cattggttct gacaagggaa    1080
caaggttatc cttccgtatt ttatggggat tactacggta tcccaaccca tggtgttccg    1140
gctatgaaat ctaaaataga ccctcttctg caggcacgtc aaacttttgc ctatggtacg    1200
cagcatgatt actttgatca tcatgatatt atcggttgga caagagaggg aaatagctcc    1260
catccaaatt caggccttgc caccattatg tcagatggtc caggtggtaa caaatggatg    1320
tatgtgggga aaaataaagc gggacaagtt tggagagata ttaccggaaa taggacaggc    1380
accgtcacaa ttaatgcaga cggatggggt aatttctctg ttaatggagg gtccgtttcg    1440
gtttgggtga agcaa                                                     1455
```

<210> SEQ ID NO 10
<211> LENGTH: 1455
<212> TYPE: DNA
<213> ORGANISM: Bacillus sp.

<400> SEQUENCE: 10

```
catcataatg ggacaaatgg gacgatgatg caatactttg aatggcactt gcctaatgat      60
gggaatcact ggaatagatt aagagatgat gctagtaatc taagaaatag aggtataacc     120
gctatttgga ttccgcctgc ctggaaaggg acttcgcaaa atgatgtggg gtatggagcc     180
tatgatcttt atgatttagg ggaatttaat caaaagggga cggttcgtac taagtatggg     240
acacgtagtc aattggagtc tgccatccat gctttaaaga ataatggcgt tcaagtttat     300
ggggatgtag tgatgaacca taaaggagga gctgatgcta cagaaaacgt tcttgctgtc     360
gaggtgaatc caaataaccg gaatcaagaa atatctgggg actacacaat tgaggcttgg     420
```

-continued

```
actaagtttg attttccagg gaggggtaat acatactcag actttaaatg gcgttggtat     480
catttcgatg gtgtagattg ggatcaatca cgacaattcc aaaatcgtat ctacaaattc     540
cgaggtgatg gtaaggcatg ggattgggaa gtagattcgg aaaatggaaa ttatgattat     600
ttaatgtatg cagatgtaga tatggatcat ccggaggtag taaatgagct tagaagatgg     660
ggagaatggt atacaaatac attaaatctt gatggattta ggatcgatgc ggtgaagcat     720
attaaatata gctttacacg tgattggttg acccatgtaa gaaacgcaac gggaaaagaa     780
atgtttgctg ttgctgaatt ttggaaaaat gatttaggtg ccttggagaa ctatttaaat     840
aaaacaaact ggaatcattc tgtctttgat gtcccccttc attataatct ttataacgcg     900
tcaaatagtg gaggcaacta tgacatggca aaacttctta atggaacggt tgttcaaaag     960
catccaatgc atgccgtaac ttttgtggat aatcacgatt ctcaacctgg ggaatcatta    1020
gaatcatttg tacaagaatg gtttaagcca cttgcttatg cgcttatttt aacaagagaa    1080
caaggctatc cctctgtctt ctatggtgac tactatggaa ttccaacaca tagtgtccca    1140
gcaatgaaag ccaagattga tccaatctta gaggcgcgtc aaaatttttgc atatggaaca    1200
caacatgatt attttgacca tcataatata atcggatgga cacgtgaagg aaataccacg    1260
catcccaatt caggacttgc gactatcatg tcggatgggc caggggggaga gaaatggatg    1320
tacgtagggc aaaataaagc aggtcaagtt tggcatgaca taactggaaa taaaccagga    1380
acagttacga tcaatgcaga tggatgggct aatttttcag taaatggagg atctgtttcc    1440
atttgggtga aacga                                                    1455
```

<210> SEQ ID NO 11
<211> LENGTH: 1548
<212> TYPE: DNA
<213> ORGANISM: B. stearothermophilus

<400> SEQUENCE: 11

```
gccgcaccgt ttaacggcac catgatgcag tattttgaat ggtacttgcc ggatgatggc      60
acgttatgga ccaaagtggc caatgaagcc aacaacttat ccagccttgg catcaccgct     120
ctttggctgc cgcccgctta caaaggaaca agccgcagcg acgtagggta cggagtatac     180
gacttgtatg acctcggcga attcaatcaa aaagggaccg tccgcacaaa atacggaaca     240
aaagctcaat atcttcaagc cattcaagcc gcccacgccg ctggaatgca agtgtacgcc     300
gatgtcgtgt tcgaccataa aggcggcgct gacggcacgg aatgggtgga cgccgtcgaa     360
gtcaatccgt ccgaccgcaa ccaagaaatc tcgggcacct atcaaatcca agcatggacg     420
aaatttgatt ttcccgggcg gggcaacacc tactccagct ttaagtggcg ctggtaccat     480
tttgacggcg ttgattggga cgaaagccga aaattgagcc gcatttacaa attccgcggc     540
atcggcaaag cgtgggattg ggaagtagac acggaaaacg gaaactatga ctacttaatg     600
tatgccgacc ttgatatgga tcatcccgaa gtcgtgaccg agctgaaaaa ctgggggaaa     660
tggtatgtca acacaacgaa cattgatggg ttccggcttg atgccgtcaa gcatattaag     720
ttcagttttt ttcctgattg gttgtcgtat gtgcgttctc agactggcaa gccgctattt     780
accgtcgggg aatattggag ctatgacatc aacaagttgc acaattacat tacgaaaaca     840
gacggaacga tgtctttgtt tgatgccccg ttacacaaca aattttatac cgcttccaaa     900
tcagggggcg catttgatat gcgcacgtta atgaccaata ctctcatgaa agatcaaccg     960
acattggccg tcaccttcgt tgataatcat gacaccgaac ccggccaagc gctgcagtca    1020
tgggtcgacc catggttcaa accgttggct tacgccttta ttctaactcg gcaggaagga    1080
tacccgtgcg tcttttatgg tgactattat ggcattccac aatataacat tccttcgctg    1140
aaaagcaaaa tcgatccgct cctcatcgcg cgcagggatt atgcttacgg aacgcaacat    1200
gattatcttg atcactccga catcatcggg tggacaaggg aagggggcac tgaaaaacca    1260
ggatccggac tggccgcact gatcaccgat gggccgggag gaagcaaatg gatgtacgtt    1320
ggcaaacaac acgctggaaa agtgttctat gaccttaccg gcaaccggag tgacaccgtc    1380
accatcaaca gtgatggatg gggggaattc aaagtcaatg gcggttcggt ttcggtttgg    1440
gttcctagaa aaacgaccgt ttctaccatc gctcggccga tcacaacccg accgtggact    1500
ggtgaattcg tccgttggac cgaaccacgg ttggtggcat ggccttga                 1548
```

<210> SEQ ID NO 12
<211> LENGTH: 1920
<212> TYPE: DNA
<213> ORGANISM: B. licheniformis

<400> SEQUENCE: 12

```
cggaagattg gaagtacaaa aataagcaaa agattgtcaa tcatgtcatg agccatgcgg      60
gagacggaaa aatcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa gcgccatatc ggcgcttttc     240
ttttggaaga aaatataggg aaaatggtac ttgttaaaaa ttcggaatat ttatacaaca     300
tcatatgttt cacattgaaa ggggaggaga atcatgaaac aacaaaaacg gctttacgcc     360
cgattgctga cgctgttatt tgcgctcatc ttcttgctgc ctcattctgc agcagcggcg     420
gcaaatctta atgggacgct gatgcagtat tttgaatggt acatgcccaa tgacggccaa     480
cattggaggc gtttgcaaaa cgactcggca tatttggctg aacacggtat tactgccgtc     540
tggattcccc cggcatataa gggaacgagc caagcggatg tgggctacgg tgcttacgac     600
ctttatgatt taggggagtt tcatcaaaaa gggacggttc ggacaaagta cggcacaaaa     660
ggagagctgc aatctgcgat caaaagtctt cattcccgcg acattaacgt ttacggggat     720
gtggtcatca accacaaagg cggcgctgat gcgaccgaag atgtaaccgc ggttgaagtc     780
gatcccgctg accgcaaccg cgtaatttca ggagaacacc taattaaagc ctggacacat     840
tttcattttc cggggcgcgg cagcacatac agcgatttta aatggcattg gtaccatttt     900
gacggaaccg attgggacga gtcccgaaag ctgaaccgca tctataagtt tcaaggaaag     960
gcttgggatt gggaagtttc caatgaaaac ggcaactatg attatttgat gtatgccgac    1020
```

-continued

```
atcgattatg accatcctga tgtcgcagca gaaattaaga gatggggcac ttggtatgcc    1080
aatgaactgc aattggacgg tttccgtctt gatgctgtca aacacattaa attttctttt    1140
ttgcgggatt gggttaatca tgtcagggaa aaaacgggga aggaaatgtt tacggtagct    1200
gaatattggc agaatgactt gggcgcgctg gaaaactatt tgaacaaaac aaattttaat    1260
cattcagtgt ttgacgtgcc gcttcattat cagttccatg ctgcatcgac acagggaggc    1320
ggctatgata tgaggaaatt gctgaacggt acggtcgttt ccaagcatcc gttgaaatcg    1380
gttacatttg tcgataacca tgatacacag ccggggcaat cgcttgagtc gactgtccaa    1440
acatggttta agccgcttgc ttacgctttt attctcacaa gggaatctgg ataccctcag    1500
gttttctacg gggatatgta cgggacgaaa ggagactccc agcgcgaaat tcctgccttg    1560
aaacacaaaa ttgaaccgat cttaaaagcg agaaaacagt atgcgtacgg agcacagcat    1620
gattatttcg accaccatga cattgtcggc tggacaaggg aaggcgacag ctcggttgca    1680
aattcaggtt tggcggcatt aataacagac ggacccggtg ggcaaagcg aatgtatgtc     1740
ggccggcaaa acgccggtga gacatggcat gacattaccg gaaaccgttc ggagccggtt    1800
gtcatcaatt cggaaggctg gggagagttt cacgtaaacg gcgggtcggt ttcaatttat    1860
gttcaaagat agaagagcag agaggacgga tttcctgaag gaaatccgtt tttttatttt    1920
```

<210> SEQ ID NO 13
<211> LENGTH: 2084
<212> TYPE: DNA
<213> ORGANISM: B. amyloliquefaciens

<400> SEQUENCE: 13

```
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtattttta tgctgtccag actgtccgct gtgtaaaaat aaggaataaa     180
gggggtgt tattatttta ctgatatgta aaatataatt tgtataagaa aatgagaggg     240
agaggaaaca tgattcaaaa acgaaagcgg acagtttcgt tcagacttgt gcttatgtgc     300
acgctgttat ttgtcagttt gccgattaca aaaacatcag ccgtaaatgg cacgctgatg     360
cagtattttg aatggtatac gccgaacgac ggccagcatt ggaaacgatt gcagaatgat     420
gcggaacatt tatcggatat cggaatcact gccgtctgga ttcctcccgc atacaaagga     480
ttgagccaat ccgataacgg atacggacct tatgatttgt atgatttagg agaattccag     540
caaaaaggga cggtcagaac gaaatacggc acaaaatcag agcttcaaga tgcgatcggc     600
tcactgcatt cccggaacgt ccaagtatac ggagatgtgg ttttgaatca taaggctggt     660
gctgatgcaa cagaagatgt aactgccgtc gaagtcaatc cggccaatag aaatcaggaa     720
acttcggagg aatatcaaat caaagcgtgg acggattttc gttttccggg ccgtggaaac     780
acgtacagtg attttaaatg gcattggtat catttcgacg gagcggactg ggatgaatcc     840
cggaagatca gccgcatctt taagtttcgt ggggaaggaa aagcgtggga ttgggaagta     900
tcaagtgaaa acggcaacta tgactattta atgtatgctg atgttgacta cgaccacccct    960
gatgtcgtgg cagagacaaa aaaatggggt atctggtatg cgaatgaact gtcattagac    1020
ggcttccgta ttgatgccgc caaacatatt aaattttcat ttctgcgtga ttgggttcag    1080
gcggtcagac aggcgacggg aaaagaaatg tttacggttg cggagtattg gcagaataat    1140
gccgggaaac tcgaaaacta cttgaataaa acaagcttta atcaatccgt gtttgatgtt    1200
ccgcttcatt tcaatttaca ggcggcttcc tcacaaggag gcggatatga tatgaggcgt    1260
ttgctggacg gtaccgttgt gtccaggcat ccggaaaagg cggttacatt tgttgaaaat    1320
catgacacac agccgggaca gtcattggaa tcgacagtcc aaacttggtt taaaccgctt    1380
gcatacgcct ttattttgac aagagaatcc ggttatcctc aggtgttcta tggggatatg    1440
tacgggacaa aagggacatc gccaaaggaa attccctcac tgaaagataa tatagagccg    1500
attttaaaag cgcgtaagga gtacgcatac gggccccagc acgattatat tgaccacccg    1560
gatgtgatcg gatggacgag ggaaggtgac agctccgccg ccaaatcagg tttggccgct    1620
ttaatcacgg acggacccgg cggatcaaag cggatgtatg ccggcctgaa aaatgccggc    1680
gagacatggt atgacataac gggcaaccgt tcagatactg taaaaatcgg atctgacggc    1740
tggggagagt ttcatgtaaa cgatgggtcc gtctccattt atgttcagaa ataaggtaat    1800
aaaaaaacac ctccaagctg agtgcgggta tcagcttgga ggtgcgttta ttttttcagc    1860
cgtatgacaa ggtcggcatc aggtgtgaca aatacggtat gctggctgtc ataggtgaca    1920
aatccgggtt ttgcgccgtt tggctttttc acatgtctga tttttgtata atcaacaggc    1980
acggagccgg aatctttcgc cttggaaaaa taagcggcga tcgtagctgc ttccaatatg    2040
gattgttcat cgggatcgct gcttttaatc acaacgtggg atcc                     2084
```

<210> SEQ ID NO 14
<211> LENGTH: 1455
<212> TYPE: DNA
<213> ORGANISM: Bacillus sp.

<400> SEQUENCE: 14

```
catcataatg gaacaaatgg tactatgatg caatatttcg aatggtattt gccaaatgac      60
gggaatcatt ggaacaggtt gagggatgac gcagctaact taaagagtaa agggataaca     120
gctgtatgga tcccacctgc atggaagggg acttcccaga atgatgtagg ttatggagcc     180
tatgatttat atgatcttgg agagtttaac cagaaggggga cggttcgtac aaaatatgga    240
acacgcaacc agctacaggc tgcggtgacc tctttaaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420
acaaagtttg attttcctgg aagaggaaat aaccattcca gctttaagtg gcgctggtat     480
cattttgatg ggacagattg ggatcagtca cgccagcttc aaaacaaaat atataaattc     540
aggggaacag gcaaggcctg ggactgggaa gtcgatacag agaatggcaa ctatgactat     600
cttatgtatg cagacgtgga tatggatcac ccagaagtaa tacatgaact tagaaactgg     660
```

-continued

```
ggagtgtggt atacgaatac actgaacctt gatggattta gaatagatgc agtgaaacat      720
ataaaatata gctttacgag agattggctt acacatgtgc gtaacaccac aggtaaacca      780
atgtttgcag tggctgagtt ttggaaaaat gaccttggtg caattgaaaa ctatttgaat      840
aaaacaagtt ggaatcactc ggtgtttgat gttcctctcc actataattt gtacaatgca      900
tctaatagcg gtggttatta tgatatgaga aatattttaa atggttctgt ggtgcaaaaa      960
catccaacac atgccgttac ttttgttgat aaccatgatt ctcagcccgg ggaagcattg     1020
gaatcctttg ttcaacaatg gtttaaacca cttgcatatg cattggttct gacaagggaa     1080
caaggttatc cttccgtatt ttatggggat tactacggta tcccaaccca tggtgttccg     1140
gctatgaaat ctaaaataga ccctcttctg caggcacgtc aaacttttgc ctatggtacg     1200
cagcatgatt actttgatca tcatgatatt atcggttgga caagagaggg aaatagctcc     1260
catccaaatt caggccttgc caccattatg tcagatggtc caggtggtaa caaatggatg     1320
tatgtgggga aaaataaagc gggacaagtt tggagagata ttaccggaaa taggacaggc     1380
accgtcacaa ttaatgcaga cggatggggt aatttctctg ttaatggagg gtccgtttcg     1440
gtttgggtga agcaa                                                      1455
```

<210> SEQ ID NO 15
<211> LENGTH: 1455
<212> TYPE: DNA
<213> ORGANISM: Bacillus sp.

<400> SEQUENCE: 15

```
catcataatg ggacaaatgg gacgatgatg caatactttg aatggcactt gcctaatgat       60
gggaatcact ggaatagatt aagagatgat gctagtaatc taagaaatag aggtataacc      120
gctatttgga ttccgcctgc ctggaaaggg acttcgcaaa atgatgtggg gtatggagcc      180
tatgatcttt atgatttagg ggaatttaat caaaagggga cggttcgtac taagtatggg      240
acacgtagtc aattggagtc tgccatccat gctttaaaga ataatggcgt tcaagtttat      300
ggggatgtag tgatgaacca taaaggagga gctgatgcta cagaaaacgt tcttgctgtc      360
gaggtgaatc caaataaccg gaatcaagaa atatctgggg actacacaat tgaggcttgg      420
actaagtttg attttccagg gaggggtaat acatactcag actttaaatg gcgttggtat      480
catttcgatg gtgtagattg ggatcaatca cgacaattcc aaaatcgtat ctacaaattc      540
cgaggtgatg gtaaggcatg ggattgggaa gtagattcgg aaaatggaaa ttatgattat      600
ttaatgtatg cagatgtaga tatggatcat ccggaggtag taaatgagct tagaagatgg      660
ggagaatggt atacaaatac attaaatctt gatggattta ggatcgatgc ggtgaagcat      720
attaaatata gctttacacg tgattggttg acccatgtaa gaaacgcaac gggaaaagaa      780
atgtttgctg ttgctgaatt ttggaaaaat gatttaggtg ccttggagaa ctatttaaat      840
aaaacaaact ggaatcattc tgtctttgat gtccccttc attataatct ttataacgcg       900
tcaaatagtg gaggcaacta tgacatggca aaacttctta atggaacggt tgttcaaaag      960
catccaatgc atgccgtaac ttttgtggat aatcacgatt ctcaacctgg ggaatcatta     1020
gaatcatttg tacaagaatg gtttaagcca cttgcttatg cgcttatttt aacaagagaa     1080
caaggctatc cctctgtctt ctatggtgac tactatggaa ttccaacaca tagtgtccca     1140
gcaatgaaag ccaagattga tccaatctta gaggcgcgtc aaaattttgc atatggaaca     1200
caacatgatt attttgacca tcataatata atcggatgga cacgtgaagg aaataccacg     1260
catcccaatt caggacttgc gactatcatg tcggatgggc caggggggaga gaaatggatg     1320
tacgtagggc aaaataaagc aggtcaagtt tggcatgaca taactggaaa taaaccagga     1380
acagttacga tcaatgcaga tggatgggct aatttttcag taaatggagg atctgtttcc     1440
atttgggtga aacga                                                      1455
```

<210> SEQ ID NO 16
<211> LENGTH: 23
<212> TYPE: DNA
<213> ORGANISM: Artificial Sequence
<220> FEATURE:
<223> OTHER INFORMATION: Primer BSG1

<400> SEQUENCE: 16

```
ccatgatgca gtattttgaa tgg                                               23
```

<210> SEQ ID NO 17
<211> LENGTH: 22
<212> TYPE: DNA
<213> ORGANISM: Artificial Sequence
<220> FEATURE:
<223> OTHER INFORMATION: Primer BSG3

<400> SEQUENCE: 17

```
gtcaccataa aagacgcacg gg                                                22
```

<210> SEQ ID NO 18
<211> LENGTH: 68
<212> TYPE: DNA
<213> ORGANISM: Artificial Sequence
<220> FEATURE:

-continued

```
<223> OTHER INFORMATION: Primer BSGM1

<400> SEQUENCE: 18

      gtcatagttt ccgaattccg tgtctacttc ccaatcccaa tcccaagctt tgccgcggaa      60
      tttgtaaa                                                              68


<210> SEQ ID NO 19
<211> LENGTH: 41
<212> TYPE: DNA
<213> ORGANISM: Artificial Sequence
<220> FEATURE:
<223> OTHER INFORMATION: Primer BSGM2

<400> SEQUENCE: 19

      ctacttccca atcccaagct ttgccgcgga atttgtaaat g                         41


<210> SEQ ID NO 20
<211> LENGTH: 27
<212> TYPE: DNA
<213> ORGANISM: Artificial Sequence
<220> FEATURE:
<223> OTHER INFORMATION: Primer BSGM3

<400> SEQUENCE: 20

      ggatgatcca tgtcaaagtc ggcatac                                         27


<210> SEQ ID NO 21
<211> LENGTH: 25
<212> TYPE: DNA
<213> ORGANISM: Artificial Sequence
<220> FEATURE:
<223> OTHER INFORMATION: Primer BSGM4

<400> SEQUENCE: 21

      ctcggtcacc acgtggggat gatcc                                           25


<210> SEQ ID NO 22
<211> LENGTH: 24
<212> TYPE: DNA
<213> ORGANISM: Artificial Sequence
<220> FEATURE:
<223> OTHER INFORMATION: Primer BSGM5

<400> SEQUENCE: 22

      ccagtttttc agctgggtca cgac                                            24
```